US008306629B2

(12) United States Patent
Mioduski et al.

(10) Patent No.: US 8,306,629 B2
(45) Date of Patent: Nov. 6, 2012

(54) HYPERTHERMIA TREATMENT SYSTEMS AND METHODS

(75) Inventors: Paul C. Mioduski, Tucson, AZ (US); Roger W. Cover, Oro Valley, AZ (US); Jerry F. Rosato, Tucson, AZ (US)

(73) Assignee: Thermosurgery Technologies, Inc., Phoenix, AZ (US)

( * ) Notice: Subject to any disclaimer, the term of this patent is extended or adjusted under 35 U.S.C. 154(b) by 833 days.

(21) Appl. No.: 12/348,884

(22) Filed: Jan. 5, 2009

(65) Prior Publication Data

US 2009/0118802 A1 May 7, 2009

Related U.S. Application Data

(63) Continuation of application No. 10/801,416, filed on Mar. 15, 2004, now abandoned.

(60) Provisional application No. 60/455,022, filed on Mar. 14, 2003.

(51) Int. Cl.
*A61F 7/00* (2006.01)
*A61B 18/04* (2006.01)
*A61B 18/12* (2006.01)

(52) U.S. Cl. .......................... 607/102; 607/100; 607/101

(58) Field of Classification Search .................... 607/102
See application file for complete search history.

(56) References Cited

U.S. PATENT DOCUMENTS

| | | | |
|---|---|---|---|
| 4,016,886 A | 4/1977 | Doss et al. | |
| 4,074,719 A | 2/1978 | Semm | |
| 4,124,030 A | 11/1978 | Roberts | |
| 4,189,685 A | 2/1980 | Doss | |
| 4,237,898 A | 12/1980 | Whalley | |
| 4,531,524 A * | 7/1985 | Mioduski | 607/99 |
| 4,644,955 A * | 2/1987 | Mioduski | 607/99 |
| 4,685,459 A | 8/1987 | Koch et al. | |
| 4,719,919 A | 1/1988 | Marchosky et al. | |
| 4,753,248 A | 6/1988 | Engler et al. | |
| 4,813,412 A | 3/1989 | Yamazaki et al. | |
| 4,867,175 A * | 9/1989 | Takase | 607/102 |
| 4,878,493 A | 11/1989 | Pasternak et al. | |
| 4,887,593 A | 12/1989 | Wiley et al. | |
| 4,907,589 A | 3/1990 | Cosman | |
| 4,920,978 A | 5/1990 | Colvin | |
| 5,183,041 A | 2/1993 | Toriu et al. | |
| 5,190,037 A | 3/1993 | Di Mino et al. | |
| 5,249,575 A | 10/1993 | Di Mino et al. | |
| 5,433,740 A * | 7/1995 | Yamaguchi | 607/102 |
| 5,484,400 A * | 1/1996 | Edwards et al. | 604/22 |
| 5,588,960 A * | 12/1996 | Edwards et al. | 604/20 |
| 5,697,925 A * | 12/1997 | Taylor | 606/34 |
| 5,743,903 A * | 4/1998 | Stern et al. | 606/31 |
| 5,755,715 A | 5/1998 | Stern et al. | |
| 5,891,134 A * | 4/1999 | Goble et al. | 606/27 |

(Continued)

*Primary Examiner* — Roy Gibson
*Assistant Examiner* — Kaitlyn Smith
(74) *Attorney, Agent, or Firm* — Robert D. Atkins; Patent Law Group: Atkins & Associates, P.C.

(57) ABSTRACT

Systems and methods are disclosed to control the temperature of an RF hyperthermia system with minimum overshoot and to improve safety by, among other things, detecting a defective temperature sensor. Temperature overshoot may be minimized by compensating for the short-term temperature difference between the area being treated and the applicator delivering the RF energy. The RF energy may heat the tissue and then the tissue may transfer heat to the applicator sensor. The system may also adapt to various applicator sizes and shapes by modifying control loop coefficients based on initial probe response.

24 Claims, 11 Drawing Sheets

U.S. PATENT DOCUMENTS

| | | | |
|---|---|---|---|
| 5,902,251 A * | 5/1999 | vanHooydonk | 600/549 |
| 6,013,074 A * | 1/2000 | Taylor | 606/34 |
| 6,066,139 A * | 5/2000 | Ryan et al. | 606/50 |
| 6,090,134 A * | 7/2000 | Tu et al. | 623/1.15 |
| 6,104,952 A * | 8/2000 | Tu et al. | 604/20 |
| 6,123,702 A * | 9/2000 | Swanson et al. | 606/34 |
| 6,162,217 A | 12/2000 | Kannenberg et al. | |
| 6,245,057 B1 | 6/2001 | Sieben et al. | |
| 6,280,441 B1 | 8/2001 | Ryan | |
| 6,304,782 B1 | 10/2001 | Van Dick | |
| 6,312,426 B1 | 11/2001 | Goldberg et al. | |
| 6,577,902 B1 * | 6/2003 | Laufer et al. | 607/102 |
| 6,818,012 B2 | 11/2004 | Ellingboe | |
| 7,022,121 B2 | 4/2006 | Stern et al. | |
| 2001/0014802 A1 * | 8/2001 | Tu | 606/21 |
| 2001/0047196 A1 * | 11/2001 | Ginsburg et al. | 607/96 |
| 2002/0058933 A1 * | 5/2002 | Christopherson et al. | 606/34 |
| 2003/0023238 A1 | 1/2003 | Manker et al. | |
| 2003/0191511 A1 * | 10/2003 | Laufer et al. | 607/99 |
| 2004/0073280 A1 * | 4/2004 | Dae et al. | 607/96 |
| 2004/0092926 A1 * | 5/2004 | Hoey et al. | 606/34 |
| 2004/0249336 A1 * | 12/2004 | Faries et al. | 604/28 |
| 2005/0015125 A1 * | 1/2005 | Mioduski et al. | 607/102 |
| 2006/0051407 A1 * | 3/2006 | Richter et al. | 424/450 |
| 2006/0122673 A1 * | 6/2006 | Callister et al. | 607/105 |
| 2006/0287649 A1 * | 12/2006 | Ormsby et al. | 606/33 |
| 2009/0118802 A1 * | 5/2009 | Mioduski et al. | 607/102 |

* cited by examiner

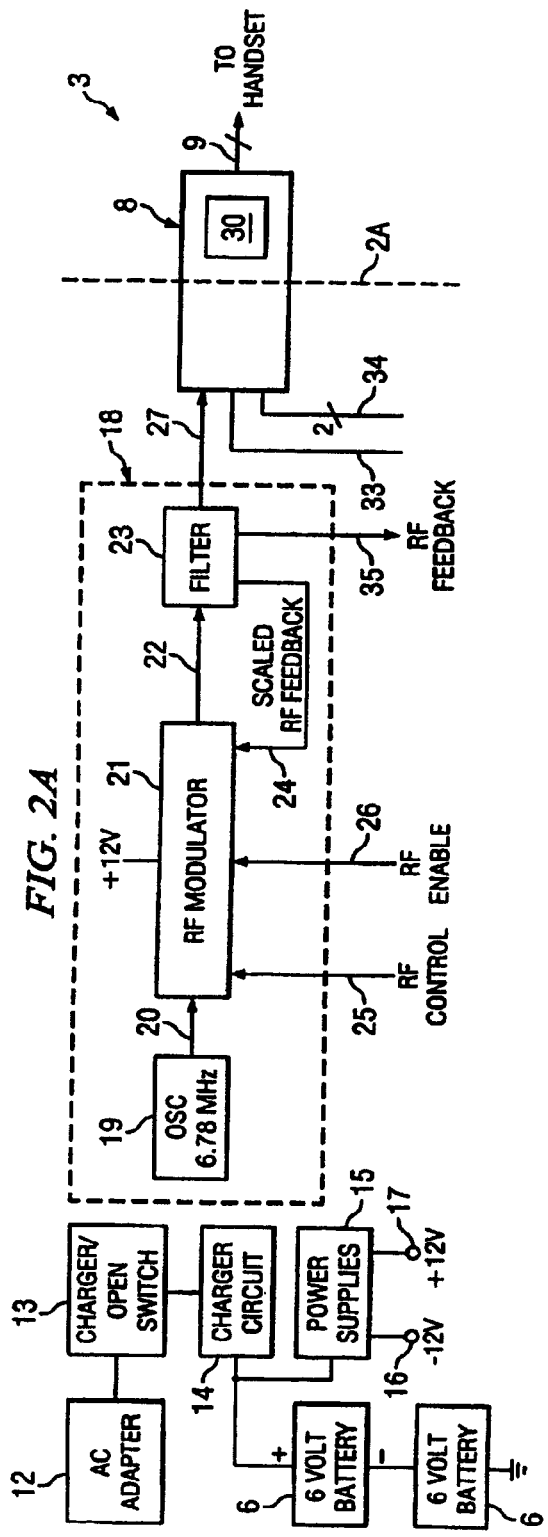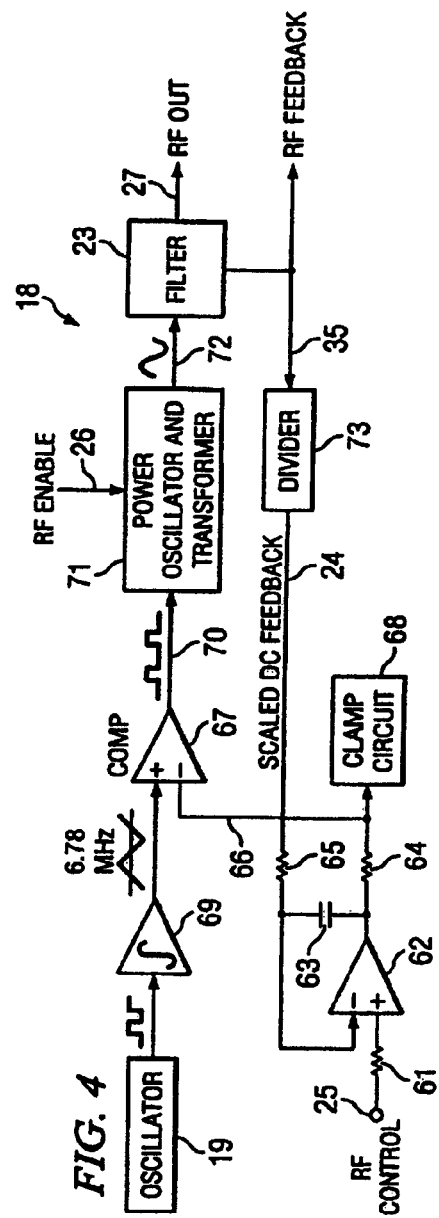

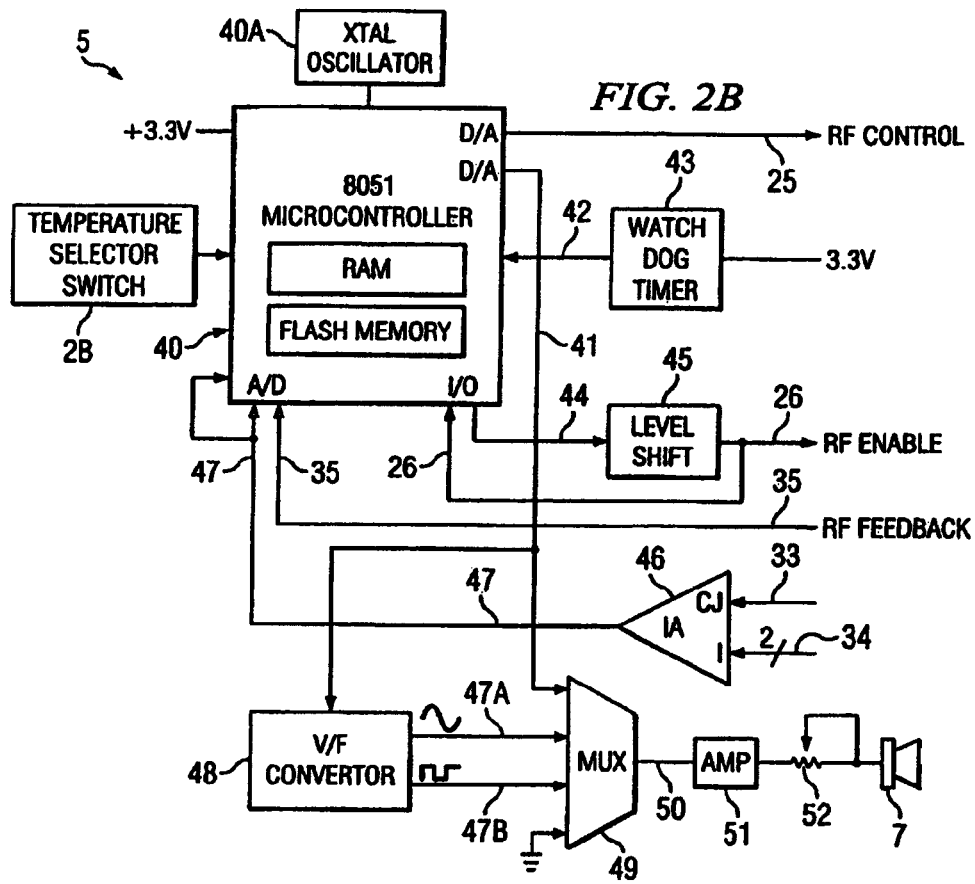

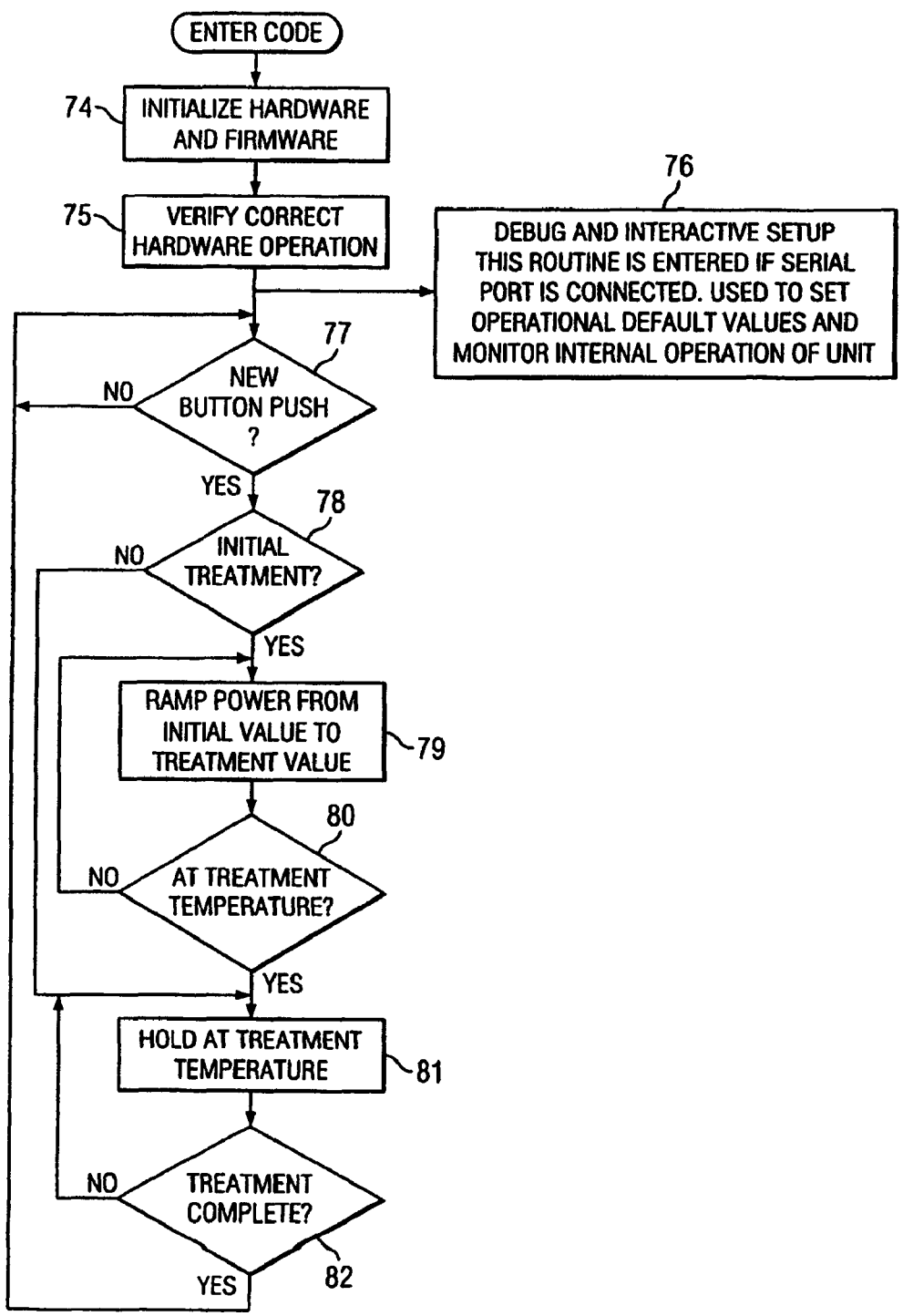

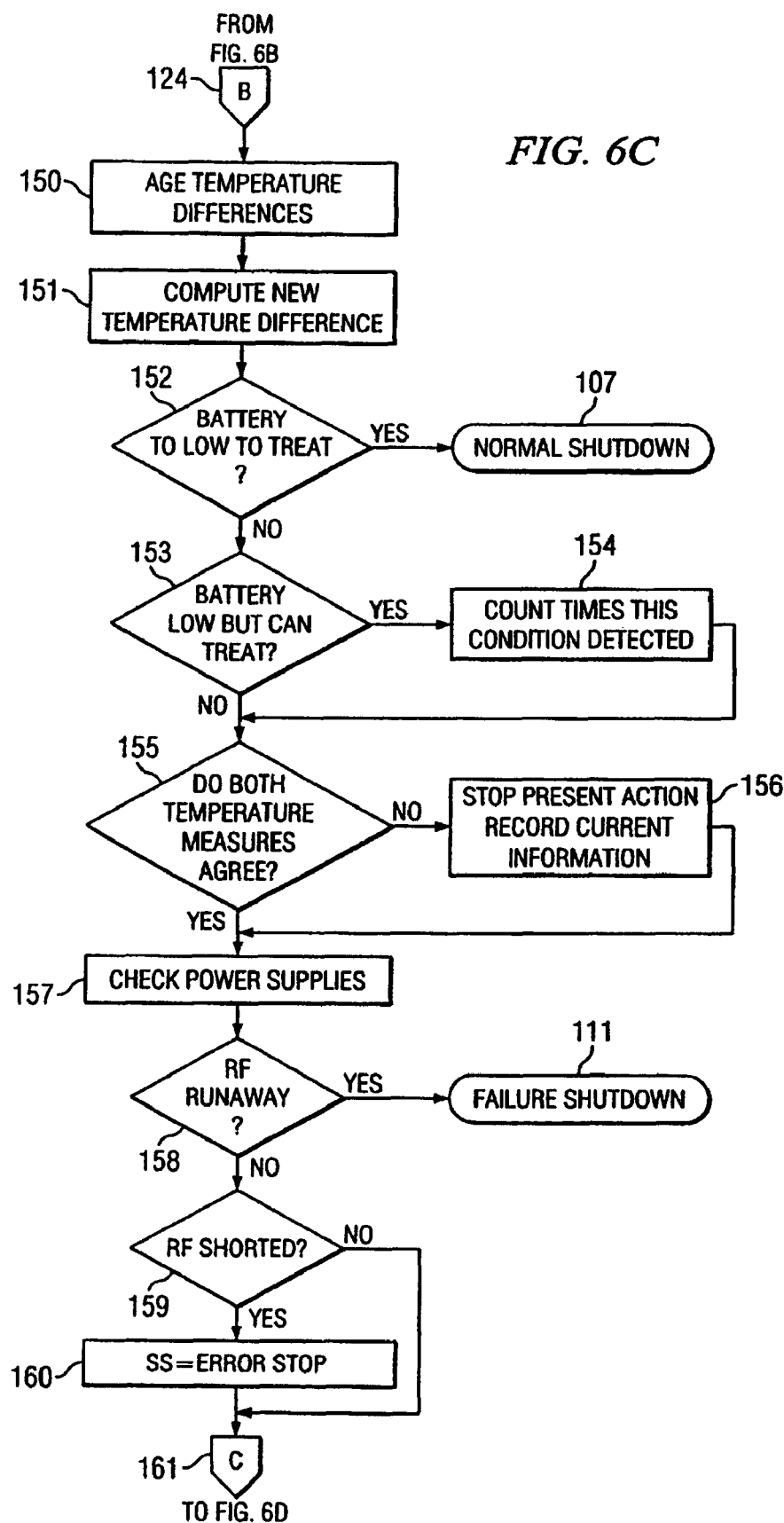

HYPERTHERMIA TREATMENT SYSTEMS AND METHODS

CROSS REFERENCE TO RELATED APPLICATION

The present application is a continuation of, claims priority to, and fully incorporates herein by reference U.S. Patent application Ser. No. 10/801,416 filed Mar. 15, 2004, which is related to, claims priority from and incorporates herein by reference U.S. Provisional Application No. 60/455,022, filed Mar. 14, 2003, entitled "HYPERTHERMIA TREATMENT SYSTEM WITH TEMPERATURE CONTROL ALGORITHM AND METHOD" by Paul C. Mioduski, Roger W. Cover and Jerry F. Rosato.

DESCRIPTION OF THE INVENTION

1. Field of the Invention

The present invention relates to medical systems and methods, and, more particularly, to hyperthermia treatment systems and methods.

2. Background of the Invention

Hyperthermia treatment systems and methods are well known for treating abnormal tissue. For example, it is well known to use such systems to apply high frequency current from a probe through the tissue under treatment to another probe, which causes the temperature of the tissue to rise to a selected level high enough to kill abnormal tissue, without permanently damaging adjacent healthy tissue.

Use of hyperthermia treatment systems and methods to noninvasively or minimally-invasively treat abnormal or malignant tissue has increased significantly in recent years. Regarding hyperthermia treatment systems and methods, studies have shown that for a specific biological effect, there is an inverse relationship between the exposure time of the treatment and the treatment temperature. For example, an increase of 1 degree Celsius to the treatment temperature may reduce the treatment exposure time to achieve a desired effect by a factor of 2. Treatment duration multiplied by the treatment temperature is known as the thermal dose. At certain thermal dose levels, abnormal tissue is affected differently than normal tissue. When heat is applied to normal tissue, blood vessels dilate, thus dissipating the heat from the tissue and preserving cellular integrity. Abnormal tissue, such as tumor tissue, has a different blood supply structure that is unable to defuse the heat as well. Thus, application of heat results in the destruction of the abnormal tissue.

U.S. Pat. No. 4,531,524 ("'524 patent"), entitled "Circuit Apparatus and Method for Electrothermal Treatment of Cancer Eye", issued on Jul. 30, 1985, to present inventor Paul Mioduski. The '524 patent discloses a hand-held electronic probe including circuitry for passing high frequency current through malignant eye tissue of livestock, or other tissue such as warts. The circuitry includes a thermistor in a probe tip that contacts the malignant eye tissue and produces a voltage that controls a voltage controlled oscillator (VCO) that drives an audio transducer. If the probe tip is held against the malignant tissue with sufficient force, the pitch of the sound emitted by the audio transducer steadily increases, indicating to the user that the proper pressure is being maintained to ensure heating of the tissue to the desired treatment temperature. The circuitry then causes the transducer to emit periodic beeping sounds which the user can count to ensure that the tissue is maintained within a desired temperature range for a desired amount of time during which the circuitry responsive to the thermistor varies the duty cycle of the high frequency current applied to the tissue so as to maintain the desired temperature within a predetermined range. Initially, high frequency current is applied at a substantially reduced duty cycle in order to prevent excessive temperature lag between the tissue and the probe tip, so as to prevent initial temperature overshoot of the tissue before the thermistor and circuitry can respond to reduce the duty cycle.

A problem with the hyperthermia treatment systems and methods disclosed in the '524 patent results from the RF energy being applied between two probes of the applicator. Specifically, there is a time lag or delay between the time at which the skin of the abnormal tissue reaches a given temperature and the time at which the thermistor in the probe detects the temperature of the abnormal tissue. This lag causes undesirable temperature overshoot of the abnormal tissue during temperature ramp-up, which can harm the patient. To compensate for such overshoot, system gain may be reduced, which eliminates or reduces temperature overshoot, but also increases the time to reach temperature, which, undesirably, increases the total treatment time. Additionally, reducing system gain limits the accuracy that can be achieved for maintaining tissue temperature at a desired level after initial ramp-up. Thus, there are difficult trade-off considerations.

It is desirable to know whether the temperature sensor in a hyperthermia system is functioning correctly. If the temperature sensor is not operating correctly, it could result in burning the patient, if the measured temperature is below the actual treatment temperature, or it could result in under-treating the patient, if the measured temperature is above the actual treatment temperature.

Some lesions are too large to fit between the RF probes, and therefore cannot be treated in a single operation cycle. Thus, a first area of the lesion is treated, and then the RF probes are moved to an adjacent, slightly overlapping region and the operation cycle is repeated. However, because the overlap treatment site is at an elevated temperature, the control loop may be unstable during the initial portion of the treatment. Depending on the amount of overlap, the hyperthermia treatment system disclosed in the '524 patent may have experienced temperature overshoot, failed to reach the preselected treatment temperature, or took too long to reach the preselected treatment temperature because its control loop was adjusted to start at a temperature of approximately 30 degrees Celsius.

Another consideration in hyperthermia treatment systems is the amount of pressure required by the applicator being used. The problem of maintaining the correct pressure on various applicators without distracting the doctor's attention from the tumor is fairly difficult. Anything that causes the doctor to inadvertently move the probes along the tumor can be very detrimental to achieving the desired treatment. But the skin may be dry, and contact pressure may be low or high, and how much power is being accepted by the tumor may not be very well known.

There is an unmet need for improved hyperthermia treatment systems and methods which address these and other considerations of the related art.

SUMMARY OF THE INVENTION

In accordance with an embodiment of the invention, a method of operating a hyperthermia treatment system is disclosed, comprising measuring a temperature that is within an allowable range of operation for the system, and determining whether to continue operation of the system based on a parameter related to the measured temperature.

In accordance with another embodiment of the invention, a medical device for performing hyperthermia treatment is disclosed, comprising a heat source for providing heat for the hyperthermia treatment, a temperature sensor for measuring temperature from the providing of heat, and a processor that determines whether to continue the hyperthermia treatment based on a parameter related to a measured temperature that is within an allowable range of operation for the device.

In accordance with a further embodiment of the invention, a method of operating a hyperthermia treatment system is disclosed, comprising performing a plurality of tests to determine whether the hyperthermia treatment system is operating properly, and terminating operation of the hyperthermia treatment system in response to failure of any test of a predefined set of the tests and preventing further operation of the hyperthermia treatment system until the hyperthermia treatment system is reset for further operation at a specified facility.

In accordance with another embodiment of the invention, a method of operating a hyperthermia treatment system is disclosed, comprising determining when the hyperthermia treatment system has provided a desired temperature for treatment, evaluating one or more criteria pertaining to a thermal dose being delivered, and terminating a treatment when evaluation of one or more of the criteria indicates undertreatment of a patient.

In accordance with another embodiment of the invention, a medical device is disclosed for performing hyperthermia treatment, comprising a heat source for providing heat for the hyperthermia treatment, a temperature sensor for measuring temperature from the providing of heat, and a processor that determines when the hyperthermia treatment system has provided a desired temperature for treatment, evaluates one or more criteria pertaining to a thermal dose being delivered, and terminates a treatment when evaluation of one or more of the criteria indicates undertreatment of a patient.

In accordance with still another embodiment of the invention, a method of operating a hyperthermia treatment system is disclosed, comprising monitoring parameters relating to operation of the hyperthermia treatment system, and playing over the system a predefined announcement when a predefined operational characteristic of the system has been detected.

In accordance with still another embodiment of the invention, a medical is disclosed device for performing hyperthermia treatment, comprising a heat source for providing heat for the hyperthermia treatment, a temperature sensor for measuring temperature from the providing of heat, and a processor that monitors parameters relating to operation of the hyperthermia treatment system and plays over the system a predefined announcement when a predefined operational characteristic of the system has been detected.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

FIG. 2A is a block diagram of an RF module and associated components from FIG. 1B, in accordance with systems and methods consistent with the present invention.

FIG. 2B is a block diagram of a microcontroller module and associated components from FIG. 1B, in accordance with systems and methods consistent with the present invention.

FIG. 3 is a schematic diagram of an applicator, a handset, and a cable of a hyperthermia treatment system from FIG. 1B, in accordance with systems and methods consistent with the present invention.

FIG. 4 is a schematic diagram of an RF oscillator, modulator, and filter circuit from FIG. 2A, in accordance with systems and methods consistent with the present invention.

FIGS. 5A and 5B are flow charts depicting methods for operating a hyperthermia treatment system, in accordance with systems and methods consistent with the present invention.

FIGS. 6A-6F are flow charts depicting in greater detail methods for operating a hyperthermia treatment system as depicted in FIGS. 5A and 5B, in accordance with systems and methods consistent with the present invention.

DESCRIPTION OF THE EMBODIMENTS

Reference will now be made in detail to the present exemplary embodiments of the invention, examples of which are illustrated in the accompanying drawings. Wherever possible, the same reference numbers will be used throughout the drawings to refer to the same or like parts.

Figure 1A:
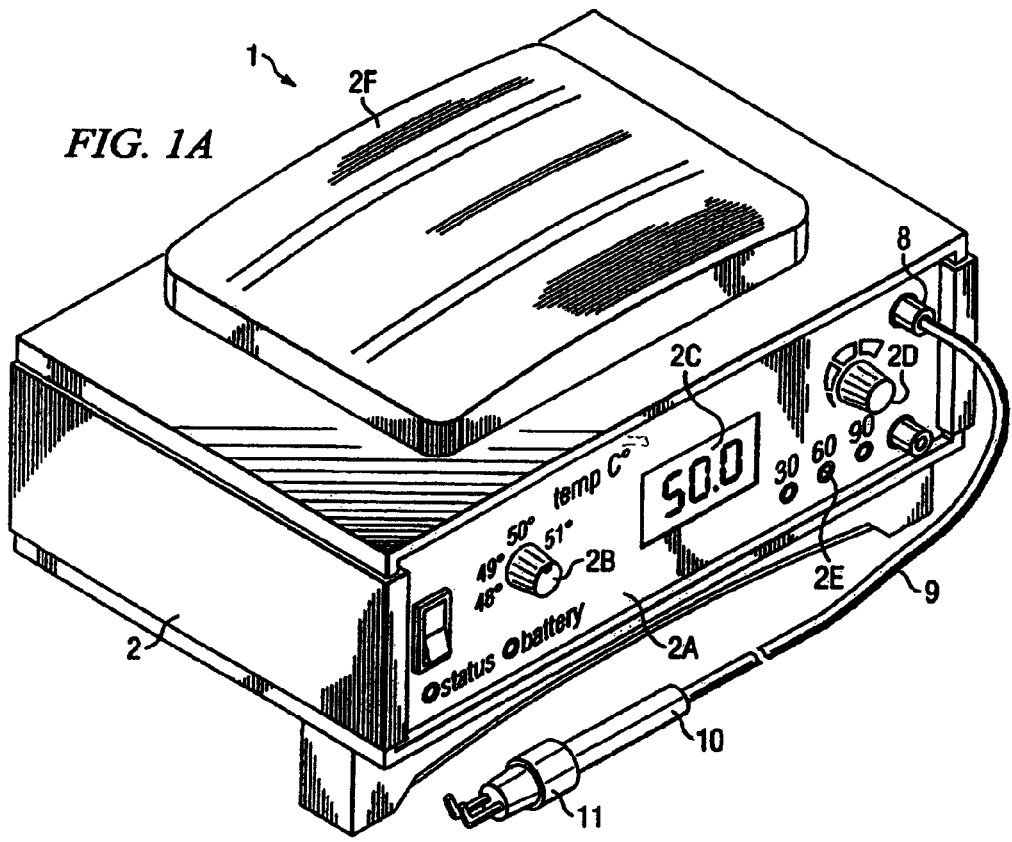
FIG. 1A is a perspective view of a hyperthermia treatment system, in accordance with systems and methods consistent with the present invention.

FIG. 1A shows a hyperthermia treatment system 1 for treating skin and/or tissue (hereafter collectively referred to as "tissue"). Tissue treatment may include treatment for any abnormality, ailment, condition, disease, disorder, wound or the like, which may include: Actinic Keratosis, Angioma, Acrochordon, Atypical Mycobacteria, Chromoblastomycosis, Cystic Acne, Clavus, Cutaneous Leishmaniasis, Dermatophytosis, Epidermoid Cysts, Fibroma, Hydrocystoma, Keloids, Molluscum Contagiosum, Mycetoma, Seborrheic Keratosis, Sporotrichosis, Syringoma and Warts.

Figure 1B:
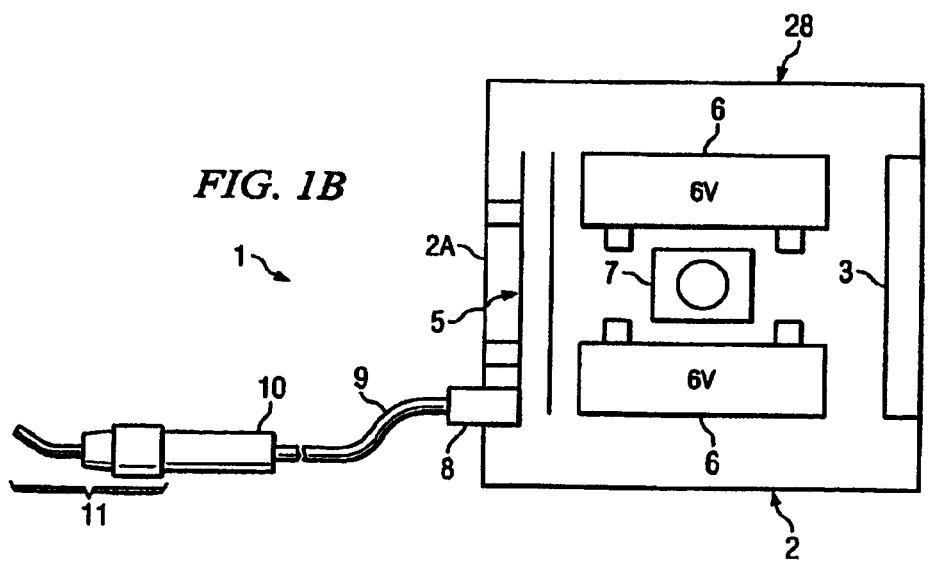
FIG. 1B is a block diagram of a hyperthermia treatment system, in accordance with systems and methods consistent with the present invention.

Hyperthermia treatment system 1 may comprise a localized current field RF instrument and may include a main unit 2 having a front panel 2A. A treatment temperature selection knob 2B may provide the function of setting a desired treatment temperature. An LCD display 2C may display a measured temperature. A sound control knob 2D may set a volume of any sound emitted by a speaker 7, as shown in FIG. 1B. A handle 2F may be provided on top of main unit 2. A conventional RF connector 8 may be connected to a cable 9, which may be connected to a handset 10. An applicator 11 may be plugged into handset 10. As described below, probes 36A and 36B (FIG. 3) of applicator 11 may be pressed against abnormal tissue (i.e., tissue of a tumor or other lesion) which may cause RF energy to be conducted from one probe through the abnormal tissue to the other probe in order to elevate the temperature of the tissue to a selected value and then maintain it at the selected value for a predetermined time. Plug-in handset 10 may accept various sized and shaped applicators 11 for various kinds of tissue.

One or more indicators, e.g., LED indicator lights 2E may perform various functions, depending on the operating mode which may include, indicating the elapsed treatment time, the level of battery charge or system self-test diagnostic results. The battery indicator mode of LEDs 2E may also indicate the approximate number of treatments that can be made on the remaining battery charge. Hyperthermia treatment system 1 may be battery-operated, to avoid any possibility of electrical shock to the patient.

Referring to FIG. 1B, hyperthermia treatment system 1 may include a main unit 2 which may include an RF module which may be 3 mounted in a rear portion of a housing 28 of main unit 2 and a microcontroller module 5 which may be mounted in a front portion of housing 28. One or more batteries 6 and a speaker 7 may be included in housing 28, as shown.

Hyperthermia treatment system 1 may use one or more temperature sensor e.g., a thermocouple 29 (FIG. 3) to measure temperature in one or more of the applicator probes to assist in controlling the amount of applied RF energy so as to control the temperature of the treatment site during temperature amp-up to a selected value and then to assist in maintaining temperature to within a range, e.g., +/−1 degree Celsius of the desired temperature for a predetermined treatment time. The treatment time may be of any desired duration, however, it is desirable to have treatment times of no more than approximately 90 seconds. Any desired treatment site temperature may be used, however, a preferred range is from 38 degrees Celsius to 65 degrees Celsius.

Hyperthermia treatment system 1 may control ramping up of the temperature of the treatment site to a selected treatment value. The pitch of an audible sound that may be produced by speaker 7 may indicate the progress of the ramp-up to the desired temperature. After the treatment site (as may be measured by thermocouple 29) reaches the preselected value, a distinct sound may be produced, such as a beep played at the same regular interval, e.g., 2 seconds for same time period, e.g., 30 seconds. After a predetermined period of time, e.g., 30 seconds with the tissue at the desired treatment temperature, a different sound, e.g., longer beeping sound may be produced. During treatment, indicator lights 2E may indicate how long the treatment site has been at the desired temperature, e.g., (30, 60, and 90 seconds).

Referring to FIG. 2A, RF module 3 may include power supply circuitry 15 that may be powered by batteries 6, which may comprise two six volt batteries connected in series and which may have been previously been charged by charger circuit 14. Charger circuit 14 may be connected by a switch 13 which may be on the rear panel of main unit 2, to an AC adapter circuit 12. A shutter which may be associated with switch 13 may prevent a battery charger (not shown) from being plugged into hyperthermia treatment system 1 while it is being used to prevent possible electrical shock to a patient due to high-voltage transients that may be present on external power lines or to a malfunction of the AC adapter. Power supply circuitry 15 may provide a +12 volt supply voltage on a conductor 17 and a −12 volt supply voltage on a conductor 16 to power the various circuits in hyperthermia treatment system 1. RF module 3 may also include RF circuitry 18 that may include a crystal oscillator circuit 19 which may produce a 6.78 MHz signal 20 which may be applied as an input to an RF modulator circuit 21, and may also include various signal conditioning circuits (not shown).

RF modulator circuit 21 may be controlled by an RF control signal 25 and an RF enable signal 26 and may produce a modulated RF signal 22 that may be applied to an input of a filter 23. Filter 23 may produce an RF output signal 27 that may be applied to a terminal of connector 8, through cable 9 and handset 10 and applied across conductive probes 36A and 36B of applicator 11. Filter 23 may produce RF feedback signal 35 which may represent the amplitude of the RF voltage on conductor 27, and may be applied as an input to a microcontroller module 5 of FIG. 2B. Filter 23 may also produce a scaled RF feedback signal 24 which may be applied to another control input of RF modulator 21. Scaled RF feedback signal 24 may be scaled-down version of RF feedback signal 35, and may be scaled down to a range that may be compatible with the range of RF control signal 25 that may represent the RF output voltage 27 being called for by microcontroller 40. As subsequently explained, the scaled RF feedback signal 24 may represent either the RF voltage (in one embodiment) or the RF power (in another embodiment) that may be applied to the treatment site being contacted by the probes of applicator 11 The oscillator output may be modulated to control the amplitude of the output 22 of RF modulator 21, which may then be filtered and transmitted to handset 10 and probes 36A and 36B.

In contrast to the related art which produces an unknown RF output voltage and only begins to reduce the power output as the selected temperature is closely approached, the disclosed embodiment of the present invention may use scaled RF feedback signal 24 with RF circuitry 18 so as to cause the voltage of the RF modulator output signal 22 to be a known quantity, regardless of the load impedance constituted by the treatment site contacted by the applicator probes and/or the impedance between the probe surfaces and the tissue. The feedback loop may regulate the amount of energy going into the RF output transformer which may produce the 6.78 MHz signal by varying the duty cycle of the signal going into the base of the output transistor, and that may allow the temperature overshoot of the treatment site to be minimized and at the same time also may allow the fastest practical ramp-up of the treatment site temperature to the preselected value. If the RF feedback circuit is not used to linearize the oscillator circuit, the ramp time may have to be extended in order to prevent temperature overshoot.

RF oscillator 19, which may be a crystal oscillator, may generate an output 20 having a frequency of 6.78 MHz, which may be an input to RF modulator 21, which may produce an RF signal 22 that may be input to filter 23. The RF control signal 25 from microcontroller 40 may establish the desired RF output signal level which may be selected by means of temperature selection knob 2B. RF enable signal 26 may be generated by microcontroller 40, which may enable or disable the RF output signal 27. The filter 23 may produce an RF feedback error signal, namely, RF feedback signal 35, that, in effect may indicate to microcontroller 40 whether the system is producing the desired output voltage. Such information may help determine whether or not good electrical and thermal contact of probes 36A and 36B is being made to the treatment site or whether there are other problems with applicator 11, such as a non-operational RF oscillator or a short circuit across the RF probe. Treatment may be automatically terminated by microcontroller 40 if the RF feedback signal 35 is not within a reasonable range.

Another approach to control of the amount of RF energy delivered to the treatment site is to sense the amount of RF power (rather than the amount of voltage) that may be delivered to and absorbed by the treatment site. This may provide better control of the amount of RF power delivered and absorbed, because it may measure the impedance of the "load" to which the RF energy may be supplied and may indicate whether more or less power should be applied by the RF circuitry 18. A multiplier circuit (not shown) may be used to compute the power delivered to the treatment site by multiplying the voltage on conductor 27 by the current through it, and the resulting value may determine the value of the signal on feedback conductor 24. Providing power feedback instead of voltage feedback may allow faster ramp-up times and lower overshoot. It may predict the rate of change of temperature by measuring the power absorption rate.

In FIG. 2A, the scaled RF feedback signal 24 may linearize the relationship of the voltage on conductor 22 to the RF control signal 25, and may substantially improve the accuracy of control of the amount of RF power delivered to the treatment site. As a result, microcontroller 40 may use the complete range of its internal D/A converters, which may improve loop stability, maximum ramp rate, and temperature accuracy when at the desired temperature.

As subsequently explained, a cold junction compensation circuit 30 may be built into connector 8. A pair of conductors 34 may be connected through corresponding terminals of connector 8 and through cable 9 and handset 10 to the terminals of thermocouple 29 which may be in RF probe 36A. A conductor 33 may be connected to the output of a conventional cold junction compensation circuit 30 and may conduct a compensation signal that may be used to adjust the thermocouple output signal 34 for the amount of offset caused by a copper-to-constantan junction of a typical type T thermocouple.

Referring to FIG. 2B, microcontroller module 5 may include a microcontroller 40, which can be an 8051 type microcontroller that may include 2 kilobytes of internal RAM, 32 kilobytes of internal nonvolatile flash memory, at least three analog-to-digital (A/D) converter channels, and at least two internal digital-to-analog converter (D/A) channels. A crystal 40A may be connected to provide a reference clock to an oscillator in microcontroller 40. Microcontroller 40 may be powered by a +3.3 volt supply voltage that may be produced by a power supply circuit (not shown) that in turn may be powered by supply voltage conductor 17 of FIG. 1B. The −12 volt supply voltage on conductor 16 may provide power for various analog circuitry. One of the D/A outputs of microcontroller 40 may be connected to RF control conductor 25. Another D/A output may be connected by conductor 41 to an input of a multiplexer 49 and to an input of the V/F converter 48. An A/D input of microcontroller 40 may be connected by conductor 47 to an output of an instrumentation amplifier (IA) 46. Another A/D input of microcontroller 40 may be connected to receive the RF feedback signal 35 from filter 23 in FIG. 2A. An I/O output of microcontroller 40 may be connected by conductor 44 to an input of a level shift circuit 45, the output of which may be connected to RF enable conductor 26. The RF enable conductor 26 also may be connected to an input of microcontroller 40.

Microcontroller 40 can run at approximately 24 MHz. It may have an internal watchdog timer (not shown) that may reset microcontroller 40 and may turn everything off if it is not accessed within a certain time. A redundant external watchdog timer 43 may also reset microcontroller 40 if watchdog timer 43 is not written to for a defined time, e.g., few tenths of a second. The internal and external watchdog timers may be powered by different power supply circuits (not shown) so that no single failure can interfere with their safety function. Microcontroller 40 may have eight A/D and two D/A terminals. One of the D/A outputs may be connected to the RF control conductor 25. That allow microcontroller 40 to set the level of the output 27 of the RF oscillator circuitry 18.

The scaled RF feedback signal 24 may be provided to linearize the RF output and thereby improve controller accuracy and reduce ramp-up time without temperature overshoot. RF feedback signal 35 may be applied to an A/D input of microcontroller 40, which may allow the microcontroller to determine whether a requested RF output voltage is achieved. The RF feedback signal 35 may be used by the microcontroller to reduce temperature overshoot and to provide safety features. If an abnormal condition, such as a short circuit across the probe electrodes or a failure in the RF oscillator occurs, microcontroller 40 can detect it and may permanently disable the unit to prevent further use. A level shifter 45 may be provided in series with RF enable conductor 26. In order to determine if the RF enable signal 26 is functioning properly, signal 26 may be fed back to an input of microcontroller 40. The purpose of level shifter 45 is to match the signal levels between microcontroller 40 which may operate at 3.3 V and the RF oscillator control circuitry which may utilize +5 volt and +8 volt power supply voltages.

Referring to FIG. 3, a cold junction offset input of instrumentation amplifier 46 may be connected to conductor 33 to receive the cold junction offset signal that may be produced by cold junction compensation circuit 30 in connector 8. The differential inputs of instrumentation amplifier 46 may be connected, respectively, to the conductors 34 which may be coupled across thermocouple 29 in FIG. 3. Cold junction compensator circuit 30 may be mounted in connector 8, and may be connected by conductors 32A and 32B to corresponding pins of the connector 8 and the output of cold junction compensator circuit 30 may be connected through conductor 33 and a terminal of connector 8 to the special compensation input terminal of instrumentation amplifier 46. The instrumentation amplifier in combination with its input filter circuitry may be a differential amplifier that may provide common mode rejection for a low voltage thermocouple signal. Most of the "common mode noise" may come from the RF generator. The output of instrumentation amplifier 46 may be coupled to two of the A/D inputs of microcontroller 40. Since the gains of the A/D converter channels may be different, this may provide a larger dynamic range, meaning that the low gain A/D channel may cover a larger temperature range, but may not have very good resolution because each bit may represent almost 0.1 degrees Celsius. The higher gain channel may have better resolution (approximately 0.05 degrees Celsius), but, may have limited temperature range. Together they may allow a wide temperature range and good resolution in a region of interest, e.g., near 50 degrees Celsius.

Either V/F converter 48 or microcontroller 40 can generate an audible tone signal that may pass through multiplexer 49, audio amplifier 51, and volume control circuit 52 to speaker 7. Multiplexer 49 may receive two of its inputs from V/F converter 48, which may have an input connected to microprocessor output 41. V/F converter 48 may produce three outputs, which may include a sine waveform, a square waveform, and a triangle waveform, the first two of which may be connected to two separate inputs, of multiplexer 49. The third input of multiplexer 49 may be connected to ground so the sound generator can be turned off when desired. The fourth input of multiplexer 49 may be connected to D/A output 41 of microcontroller 40, which may allow preselected or arbitrary sound waveforms generated by microcontroller 40 to be applied to speaker 7. Since the input of microcontroller 40 may be connected to output of the compensated instrumentation amplifier output 47 which may represent the temperature measured by thermocouple 29, microcontroller 40 may have information to produce an output voltage at D/A converter 41 so that the pitch of the sound produced by speaker 7 may be proportional to the temperature of thermocouple 29 and therefore to the temperature of the treatment site being heated by RF energy from probes 36A and 36B.

The V/F converter may have internal parameters that set the output frequency to between about 600 Hz and 3000 Hz. The availability of sine and square wave shapes may allow microcontroller 40 to create different sounds to alert the user of various conditions.

Referring to FIG. 3, cable 9 may connect some of the terminals of connector 8 to handset 10. Specifically, the RF output of filter 23 may be coupled through connector 8 and may become the center conductor of a coaxial cable that may have a grounded shield conductor 27A. The center conductor or "hot" conductor 27 of the coaxial cable may be connected through handset 10 and the body 11A of applicator 11 to conductive probe 36A of applicator 11. The shielded conductor 27A of the coaxial cable may be connected to the other conductive probe 36B. Thermocouple 29 may be located in probe 36A, and may have its two conductors coupled to the above-mentioned pair of conductors 34, which may extend through cable 9 to connector 8 and to the differential input terminals of instrumentation amplifier 46 of FIG. 2B.

A momentary switch 58 in handset 10, which may be utilized to start a hyperthermia treatment, and also may be used by the operator to halt the hyperthermia treatment after the desired treatment time interval has elapsed, may be connected to conductors 58A and 58B which may extend through connector 8 to microcontroller 40. A light emitting diode 59 on handset 10 may be similarly connected by conductors 59A and 59B which may extend through connector 8 to microcontroller 40 and its output buffer. LED 59 may be used to indicate the start of the treatment and to provide a visual indication of the elapsed time by blinking at same predefined frequency, e.g., every two seconds.

Note that thermocouple 29 may be mounted in the same probe 36A that may be connected to the hot conductor 27, in order to ensure that the temperature may be properly sensed even if the ground electrode may not be firmly in contact with the skin. It has been observed that heating of the treatment site can occur, under certain conditions, even if probe 36B is not in direct contact with the tissue being treated. This means that thermocouple 29 should be mounted in probe 36A. It should be understood that there may always be some capacitive coupling to the skin even if the ground electrode is not firmly in contact with the tissue. This may allow heating to take place without accurately sensing the temperature if the thermocouple was located in the ground electrode. Such heating does not occur if the high-voltage electrode is in poor contact with the skin because the capacitive coupling may be much lower.

Referring to FIG. 2A, the RF circuitry within dashed line 18 may be electrically shielded to prevent EMI (electromagnetic interference). This RF circuitry is shown in detail in FIG. 4 and may include a conventional 6.78 MHz crystal oscillator 19 that may produce a square wave output applied to the input of an integrating circuit 69. Integrating circuit 69 may produce a sawtooth waveform which may be applied to the positive input of a comparator 67 that may compare the sawtooth waveform to a reference voltage applied to the negative input of comparator 67 by means of a conductor 66. The output of comparator 67 may be a pulse signal and, the width of each pulse thereof may be determined by a comparison of the sawtooth waveform with the above-mentioned reference voltage on conductor 66. The portion of FIG. 4 other than power oscillator and RF output transformer circuit 71 and filter 23 is the RF modulator 21 of FIG. 2B. The resulting duty-cycle-modulated RF signal on conductor 70 may be applied as an input to a conventional RF power oscillator circuit 71 which may produce an output 72 that may be filtered by filter circuit 23 to produce a sinusoidal waveform. RF enable conductor 26 may be connected to an input of power oscillator circuit 71. Power oscillator circuit 71 may include an RF output transformer, the secondary winding of which may be connected to conductor 72. Filter circuit 23 may produce a 6.78 MHZ RF signal RFOUT proportional to the value of the RF Control signal 25.

An RF feedback signal 35 may be produced by filter 23 and may be divided by a divider circuit 73 to produce the above-mentioned scaled RF feedback signal 24. Filter 23 may be a standard R/C filter/divider following a rectifier that may convert the RF signal to a DC signal. After the filter, the signal may be a scaled RF feedback signal 24 that may be applied through a resistor 65 to the negative input of an operational amplifier 62 and to one terminal of a feedback capacitor 63, the other terminal of which may be connected to the output of operational amplifier 62. The output of operational amplifier 62 also may be connected to one terminal of resistor 64, the other terminal of which may be connected by conductor 66 to the negative input of comparator 67 to provide the above mentioned reference voltage. The reference voltage on conductor 66 also may be limited by a clamp circuit 68. The positive input of operational amplifier 62 may be coupled by resistor 61 to RF control signal 25 in order to set the desired temperature at which the abnormal tissue may be maintained during the treatment operation. The RF enable signal 26 may be driven by microcontroller 40 through a level shifting circuit 45 shown in FIG. 2B.

The operator can perform an independent temperature verification by putting the hyperthermia treatment device 1 into an "operate" mode, in which case the readout 2C may indicate the present room temperature. The readout may always read the temperature of the applicator electrode. This may be true before and after treatment. This continuous display is intended as an additional safety feature that may allow the operator to determine if the system is behaving properly.

During a treatment the self-test algorithm that may be executed by microcontroller 40 may require that during a first period, e.g., a first four second interval, there must be an increase of a predetermined amount, e.g., 0.4 degrees Celsius of thermocouple 29 from a previously measured temperature. To accomplish this, the self-test program may continue to acquire a sequence of "local minimum temperatures" and require that there be at least a 0.4 degree Celsius rise in the temperature of thermocouple 29 from at least one of the local minimum temperatures acquired during the first four second interval. The self-test algorithm may require that there be an increase of at least 0.4 degrees Celsius from the lowest accumulated local minimum temperature during the first four seconds to verify that thermocouple 29 is operating correctly. The hyperthermia treatment may be terminated if either 1) the thermocouple temperature does not undergo a temperature increase of at least 0.4 degrees Celsius during the first four seconds of the self-test procedure, or 2) the thermocouple temperature does not rise above the initial thermocouple temperature by the end of the first eight seconds of the self-test procedure. Also, the above algorithm may detect a malfunction of thermocouple 29 even if it occurs during a hyperthermia treatment cycle. The program may conclude that thermocouple 29 is malfunctioning if either or both requirements are not met.

If the present cycle of the hyperthermia treatment process has just been completed on the first portion of a large lesion, and a second cycle of the hyperthermia treatment process is about to begin on a second portion of the lesion that slightly overlaps the first portion, the tissue may already be quite warm from the first treatment cycle. It is desirable to know whether a temperature drop of thermocouple 29 after the beginning of the second cycle is a normal temperature decrease due to a high initial temperature caused by RF heating from the first cycle or whether the thermocouple is malfunctioning after the RF probes have been moved to a new tissue area. By looking at the change in the rate of change of the temperature before and after the RF oscillator is enabled, microcontroller 40 can determine if the high temperature start is a result of an overlap procedure or a malfunctioning thermocouple. The algorithm may require an absolute temperature change of at least 0.4 degrees Celsius during the first 4 seconds of the treatment or a relative change of 1 degree Celsius during the first 8 seconds.

The self-test algorithm and the temperature control algorithm may be executed by microcontroller 40 to prevent hyperthermia treatment system 1 from applying RF energy to a treatment site below 20 degrees Celsius mainly as a test to detect any flaw in thermocouple 29 or a malfunction of temperature compensation circuit 30.

Having the start temperature above a predefined minimum temperature, e.g., 20 degrees Celsius may allow detection of a malfunctioning thermocouple and/or a malfunctioning cold junction compensation circuit. A thermocouple is a metal-metal junction which may generate a small magnitude open circuit voltage signal (e.g., tens to hundreds of millivolts) that may be generally proportional to temperature and can be measured by a bridge circuit or an instrumentation amplifier. The cold junction in the above-described system may be located in the connector 8, which is why the cold junction compensation circuit may also be located therein, and it may require a cold junction compensation circuit, because the cold junction produces another voltage that may tend to offset the voltage produced by thermocouple 29 and therefore may produce a temperature measurement error. Cold junction compensation circuit 30 may produce an offset voltage that may be proportional to the cold junction voltage and may compensate it by providing an offset signal to the instrumentation amplifier that may be used to measure the voltage produced by thermocouple 29, and thereby may avoid an error, e.g., 25 degrees Celsius, in the room temperature reading. A start temperature above 20 degrees Celsius may allow easy determination as to whether there is a shorted thermocouple or a defective cold junction compensation circuit. If either occurs, the temperature may read near a minimum value, e.g., approximately 10 degrees Celsius. If the thermocouple is defective (open), the temperature signal from the thermocouple may approximate a maximum temperature value, e.g., approximately 65 degrees Celsius.

The self-test algorithm may also determine whether the temperature of thermocouple 29 attained a selected desired treatment temperature within a pre-determined time, e.g., 45 seconds, and if this determination is affirmative, the algorithm may conclude that hyperthermia treatment system 1 is functioning properly. Hyperthermia treatment system 1 may allow the physician a predetermined time, e.g., 15 seconds, to begin a next treatment without retesting the thermocouple 29. This may allow a reasonable overlap of the present treatment cycle with a previous treatment cycle, which may be desirable for some procedures.

To ensure that the system is operating safely, the self-test algorithm may perform a plurality of independent temperature tests. Comparator circuitry internal to the microcontroller may be programmed to permanently shut down the system if the temperature exceeds a predetermined maximum value, which may be approximately 58 degrees Celsius. The algorithm may also require that after reaching a desired treatment temperature the unit must remain within a predetermined temperature window, which may be determined from a table of values. The table may allow the system to react faster if the temperature error is large. As an additional safety measure, a set of comparators external to the microcontroller may also have the ability to disable the system if the temperature exceeds a predetermined value, e.g., 58 degrees Celsius. These external comparators may provide a backup in case the microcontroller malfunctions. Also, the self-test algorithm may operate to detect whether: (1) a power supply is out of specification by reading the value of each power supply using its internal A/D converter, (2) the timer is working properly as determined by the internal and external watchdog timers, and/or (3) the redundant ADC converter inputs match. If any of these or other suitable determinations are affirmative, microcontroller 40 may permanently disable hyperthermia treatment system 1 to ensure that it cannot be used again unless and until it is sent back to the factory for repair and/or replacement.

Initially, after waiting for oscillator 19 to start up, the system may perform a self test operation (which actually may be repeated at some predetermined interval, e.g., approximately every 50 milliseconds), during which everything may be held inactive until it may be determined that the microcontroller oscillator started properly. If the RF circuitry 18 does not start up properly within a predetermined time, e.g., 1.5 seconds, the unit may be set into a permanently disabled mode and returned to the factory for repair or replacement.

The hyperthermia treatment system 1 may have a plurality of states. A first state may be "normal operation", a second state may be for "treatment operation" or "standby operation" and a third state may be "abnormal operation," which may include a first condition that may require stopping a current hyperthermia treatment, and a second condition that may require that hyperthermia treatment system 1 be set to a disabled state and returned to the factory before it can be used again for hyperthermia treatment. Hyperthermia treatment system 1 may be disabled and returned to the factory whenever a condition is detected which could result in a risk to a patient, irrespective of whether hyperthermia treatment system 1 might be operational if it is turned off and then powered up again.

The self-test operations may include testing power supply voltages, doing A/D converter input comparisons and D/A converter output comparisons, one against the other, to determine if they are working properly, determining if the oscillators 19 and 40A are operating properly, determining if their frequency ratio is approximately correct to establish whether either is substantially off frequency, and testing some I/O bits, which may include the RF enable. Some or all of the self-test operations may be performed on a continuous basis over some predetermined interval (in this case every 50 milliseconds), and if any critical self-test fails more than a predefined limit, e.g., three times in a row, then hyperthermia treatment system 1 may be set in the "disable and return to factory" mode. The present treatment may be terminated if any self-test operation fails only once. The setting of treatment temperature selection knob 2B may be read, any "off" transition of the power on-off switch may be detected, and the battery test may be determined, all by microcontroller 40.

Microcontroller 40 may also set the state of the 30/60/90 second LEDs 2E, which may be used primarily to indicate battery charge level and elapsed treatment time, but may also be used for diagnostic purposes. During a battery test, the 30/60/90 second LEDs not only may indicate the percentage of battery charge remaining, they may also indicate the approximate number of remaining treatments that can be performed with the remaining battery charge, because the fully charged battery may be capable of powering hyperthermia treatment system 1 for approximately 100 hyperthermia treatments. In the "treatment timing mode" the LEDs 2E may indicate to the physician the elapsed treatment time, e.g., 30 seconds, 60 seconds, or 90 seconds, so that the physician can terminate the present treatment by depressing momentary switch 58 of handset 10 at the time they determine to be appropriate.

Hyperthermia treatment system 1 may begin operation at reduced power. The reason for this is that there may be a long lag between the time at which the treatment site is heated up to the desired treatment temperature by the applied RF energy and the time at which thermocouple 29 actually detects the heating. The treatment site could be burned before the correct temperature could be determined from the thermocouple if hyperthermia treatment system 1 were to be started at full power. By starting the temperature ramp-up procedure at a predetermined reduced power level, e.g., about 30 percent, of the maximum RF output voltage on conductor 27 and ramping to 100 percent (if required) may allow the treatment temperature to be achieved within a predetermined period, e.g., approximately 20 seconds. This may be achieved by using a PID loop algorithm that may generate the RF control signal by summing the integral gain, a derivative gain, and proportional gain. Other parameters may be used which are not typically used in PID loops. One may be that the selected treatment temperature, plus or minus a predetermined temperature, e.g., one degree Celsius, must be attained within a predetermined time, e.g., 45 seconds, and if more time is required to ramp up to the selected temperature, the treatment may be automatically terminated. Typical ramp up times may be approximately 20 seconds.

PID loop software, as represented in the subsequently-described flowchart, may determine the error between the desired treatment temperature and the actual temperature of the treatment site, and may multiply that difference by the proportional gain term in order to obtain a proportional gain value. Specifically, the PID loop integrate the difference over time, and then multiply that by the integral gain term to obtain an integral value. The PID loop may determine the derivative of that difference and multiply it by the differential gain term to obtain the differential gain value, and then may sum all three together and output that value to the RF control signal 25 through a D/A converter of microcontroller 40. With integral gain, if the preselected temperature is not being achieved, i.e., the overall system does not have enough gain, the integral gain may be increased in accordance with the amount of time required to achieve the preselected temperature. The integral gain may force the RF output signal to the value needed regardless of the value of the proportional gain. The opposite condition can occur when the load, i.e., the treatment site, absorbs too much RF power too quickly and the treatment site heats too rapidly. In this case, the derivative term may determine how quickly the actual treatment site temperature approaches the preselected treatment temperature, and if that is occurring too rapidly, the derivative term may cause the amount of RF energy applied to the treatment site to be reduced, or cause the amount of RF energy applied to the treatment site to be increased if the actual temperature of the treatment site approaches the preselected desired treatment temperature too slowly.

Testing of the described embodiment of the invention indicates that thermocouple 29 measures treatment site temperature overshoot of less than one degree Celsius under all conditions with all available applicators and that the temperature ramp-up time of the treatment site occurs within about 20-22 seconds.

If the thermocouple temperature begins to drift outside of the plus/minus 1 degree Celsius range, a sliding scale may be used to determine how soon to terminate a treatment. If the temperature varies by more than a predetermined amount from a predetermined set point for more than a predetermined amount of time, the proper thermal dose will not be provided, and the system may alert the doctor by terminating the treatment early and making an "abnormal termination" audible sound. The sliding scale may be determined by a time/temperature matrix, which may be programmed into the microcontroller. In this embodiment, if the actual treatment site temperature is more than a predefined amount, e.g., one degree Celsius, below the preselected treatment temperature, it has to remain more than one degree Celsius below the preselected treatment temperature more than a predefined period of time, e.g., 16 seconds, before the present treatment may be terminated. If the actual treatment site temperature is more than two degrees Celsius below the preselected treatment temperature, it has to remain more than a predetermined amount, e.g., two degrees Celsius, below the preselected treatment temperature for at least eight seconds before the present treatment may be terminated.

Hyperthermia treatment system 1 may be set in the return-to-factory mode if a hardware malfunction is detected. Usually the problem that causes a treatment to be terminated is that the temperature doesn't ramp up properly, for example, because of dry skin or improper probe contact. Since the effectiveness of hyperthermia treatment may drop by a factor of two for every one degree Celsius reduction in temperature, failure of the abnormal tissue to reach the preselected treatment temperature may result in ineffective treatment.

The present device may be fully digitally controlled, which may improve system accuracy and control.

System 1 may employ methods to control the applied temperature with minimum overshoot and to improve safety by detecting any defective temperature sensor in the applicator. Such method may minimize overshoot by compensating for the short-term temperature difference between the area of the body being treated and the applicator delivering the RF energy. The RF energy may heat the treatment site and then the treatment site may transfer heat to the applicator sensor. Time lag between heating and sensing may contribute to temperature overshoot.

Another cause of overshoot may be that different applicator sizes and shapes heat treatment sites at different rates and to different depths. Methods employed by system 1 may adapt to the various applicator sizes and shapes by modifying the control loop coefficients based on the initial probe response. This may improve temperature control accuracy and further reduce temperature overshoot.

The algorithm may also use the initial probe response to detect a defective temperature sensor by comparing the rate of change in temperature before and after power is applied. A shorted thermocouple sensor, for example, can report the temperature of the cold junction compensation circuit that may be approximately at room temperature. Undetected, this could lead to over treatment or burning of the tissue being treated. The problem may be complicated by the fact that at various times in a treatment the temperature sensor can legitimately report any value between room temperature and the selected temperature because it could be cooling down from a previous treatment. By looking for changes in the rate of change of temperature before and after power is applied a defective sensor can be detected under a very wide range of conditions without false positives.

Figure 5B:
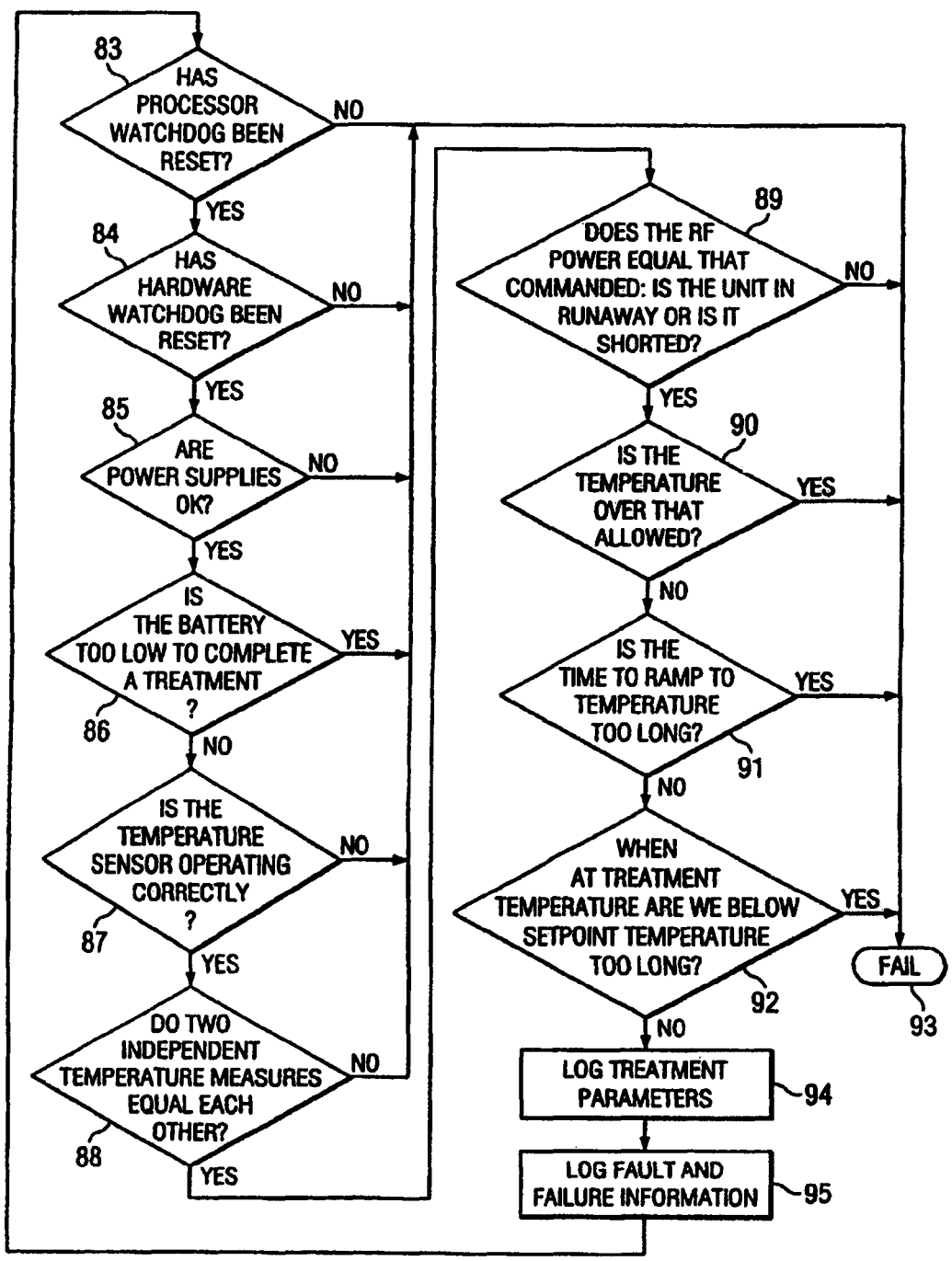

Referring to FIGS. 5A and 5B, the program in microcontroller 40 may initialize the hardware and firmware in block 74 and perform a self testing operation in block 75. Block 76 may represent a routine that can be utilized to perform debugging and interactive set-up operations. In decision block 77, the program may determine whether momentary switch 58 has been pressed, and if that determination is affirmative, the program may determine if there has been a previous hyperthermia treatment within a predetermined time period, e.g., the past 15 seconds. If this determination is negative, the program may operate to maintain the treatment site at the selected treatment temperature, as indicated in block 81. The operation implemented by decision block 78 may allow convenient treatment of overlapping regions of the abnormal tissue without starting over and performing a new ramp-up operation.

If the present treatment is considered to be an initial treatment, then the program may go to block 79 and execute a routine to ramp the power from an initial value up to the selected treatment value, as previously described. In decision block 80, the program may determine if the thermocouple is at the selected treatment temperature, and if this determination is affirmative the ramp-up operation may be completed, and in the routine of block 81, the program may operate to maintain the thermocouple at the selected treatment temperature. If the decision of block 80 is negative, the ramp-up operation of block 79 may continue. In decision block 82, the program may determine if the present hyperthermia treatment is complete, and if it is not, the program may continue to maintain the thermocouple and the treatment site at the selected treatment temperature, but otherwise the program may return to decision block 77 and await a new signal from momentary switch 58.

During the operation indicated in FIG. 5A, microprocessor may repeatedly execute the routine shown in FIG. 5B to perform concurrent error checking and data recording operations. In FIG. 5B, if any of the conditions indicated in blocks 83-92 is met, the present treatment may fail. Some of the aforementioned blocks, namely, blocks 83-85, 88 and 89, may indicate failures from which the hyperthermia treatment system 1 cannot recover without repair from the manufacturer. If the conditions indicated in any of these particular blocks occur, the operation of hyperthermia treatment system 1 may be "permanently" disabled until it has been reset by qualified repair personnel.

Figure 6A:
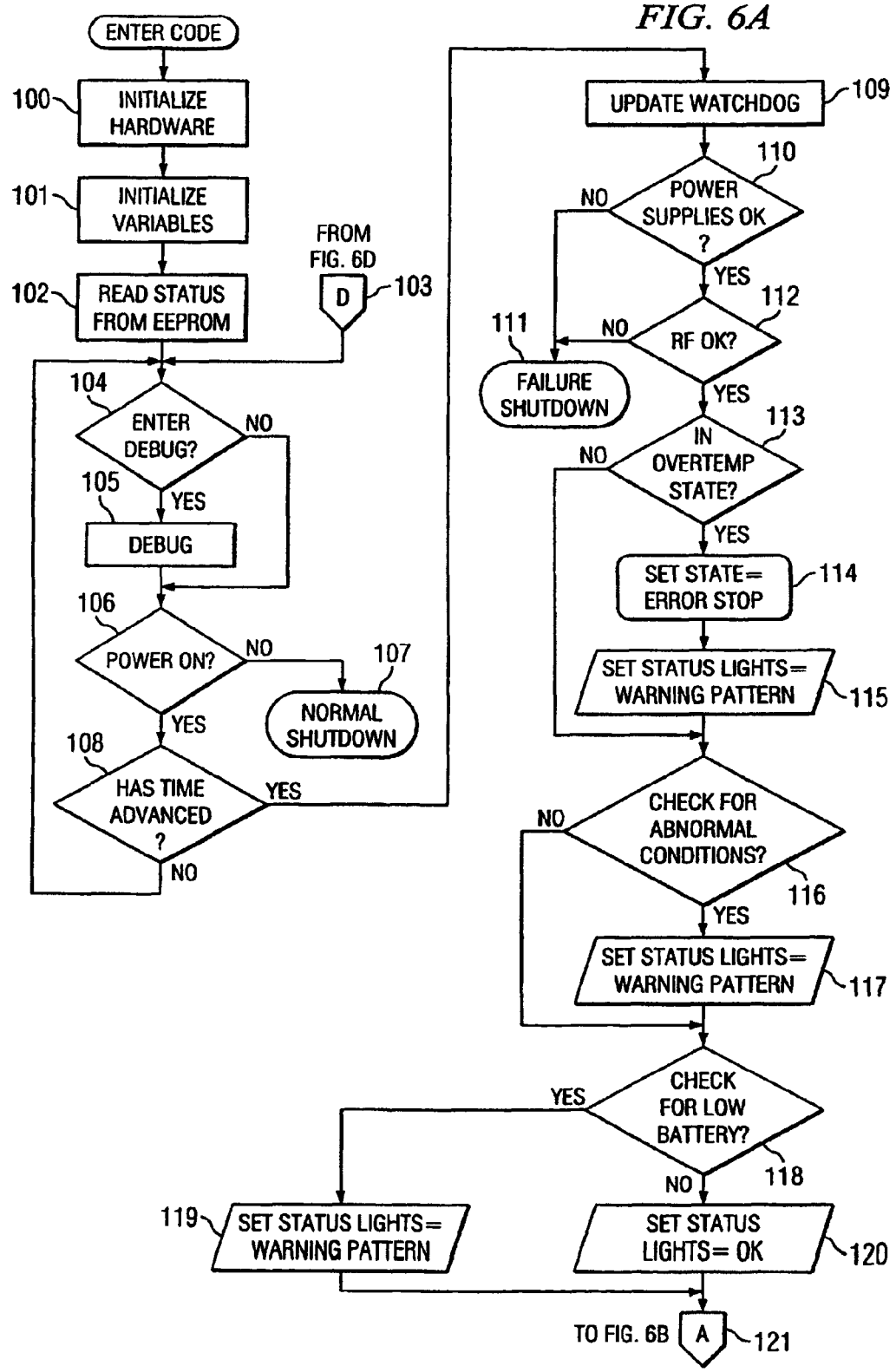

Referring to FIG. 6A, the system initially may be in a reset state, and the first step, in block 100 may be to execute a hardware initialization routine which may (include initializing registers, setting input/output buffer data directions, setting A/D converter gains, etc.), and then set up operating variables as indicated in block 101. The next step may be to read various variables and status information from the EEPROM, as indicated in block 102. Decision block 4 may allow a determination to be made as to whether to execute a debug routine (not described) indicated in block 105. If no debug routine is to be executed, decision block 106 may determine whether the power to hyperthermia treatment system 1 should continue to be on, and if it is, the program may execute a normal shutdown as indicated in block 107 in response to actuation of the power switch.

Decision block 108 may determine if a timer has timed out, and if that decision is negative, the program may reenter decision block 104. This may allow hyperthermia treatment system 1 to automatically turn itself off if no activity occurs for a predetermined period, e.g., 15 minute interval. If the timer of decision block 108 has timed out, the program may update the watchdog timer, as indicated in block 109. This may occur at some predefined interval, e.g., approximately every second.

The program may then operate to check the power supplies in hyperthermia treatment system 1 and make a decision in block 110 to execute a failure shutdown as indicated in block 111 if the power supplies are not functioning properly, and otherwise may go to decision block 112. A failure shutdown may result in disabling hyperthermia treatment system 1 until it has been repaired by the factory or by authorized personnel. Next, the program may determine in decision block 112 if the RF circuitry is functioning properly, and hyperthermia treatment system 1 may undergo a failure shutdown if the determination is negative. Otherwise, the program may go to decision block 113 and determine if the thermocouple indicates a thermocouple temperature greater than a predetermined number of degrees Celsius above the selected treatment temperature. If there is such an over-temperature condition, the program may set an "error stop" condition as indicated in block 114 and cause a specific pattern of the status LEDs 2E (FIG. 1A) to indicate the over-temperature state. If the determination of decision block 113 is negative, the program may go to decision block 116 and check for the existence of a number of predetermined abnormal conditions. If any of them are found, the program may set status LEDs 2E to a corresponding warning pattern, as indicated in block 117. The program may then go to decision block 118 and check to determine if the battery output voltage is low, and if it is, may execute a subroutine that sets the LED status lights 2E to a corresponding warning pattern and then may go to program entry point or label 121. If the battery voltage is not low, the program may set the status lights pattern to indicate acceptable battery voltage as indicated in block 120, and then may go to entry point 121.

Figure 6B:
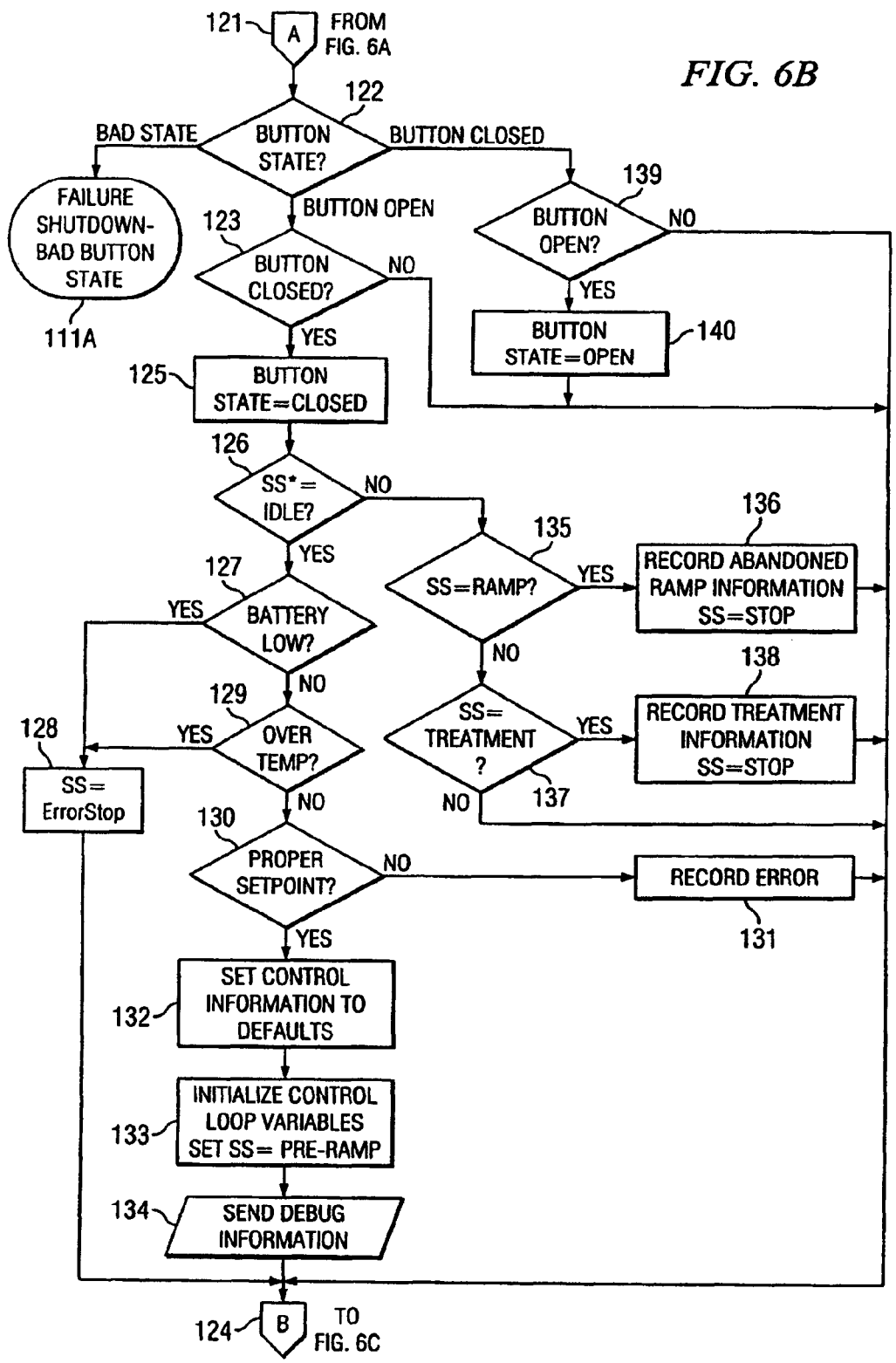

The program may then go to decision block 122 of FIG. 6B. Decision block 122 may determine which state of a plurality of possible states (e.g., switch open, switch closed, or "bad state") momentary switch 58 is presently in, and may determine an "on" code in a register if momentary switch 58 is open, an "off" code if momentary switch 58 is closed, and any other code in the register may be considered to be a "bad state" code.

As mentioned above, decision block 122 may be a multi-state conditional test that may determine which one of several conditions momentary switch 58 is in. "Button open" and "button closed" may be variables stored in a register, and a "bad state" may represent a possibly corrupted value in the register and may be any possible value in the register other than the two permitted states representing "button open" and "button closed". This may represent a fatal condition, which may necessitate disabling the system.

If the "button open" state is detected by decision block 122, the program may go to decision block 123 and, if momentary switch 58 is closed, detects a "button closed" condition as the result of a transition from the button open condition to the button closed condition, and then goes to block 125 and sets the button state as closed, and then goes to decision block 126. If a button closed condition is not detected in decision block 123, the program goes to FIG. 6C via entry point 124.

Decision block 126 of FIG. 6B may determines if microcontroller 40 is in an idle state, and if it is not, the program may determine in decision block 135 if the program is in a ramp-up state, and if that determination is negative, the program may go to decision block 137 and determine if hyperthermia treatment system 1 is in a treatment mode. If the program is determined in decision block 126 to be in an idle mode, the program may go to decision block 127 and check the battery voltage. If the battery voltage is low, the program may go to block 128 and set the system state to an "error stop" state and then go via entry point 124 to FIG. 6C. If the battery voltage is not low, the program may go to decision block 129 and determine if the thermocouple temperature is at an excessively high temperature, and if this determination is positive, the program may go to block 128 and set the system state to an error stop condition to terminate the present treatment (but may not permanently disable hyperthermia treatment system). If the determination of block 129 is negative, the program may go to decision block 130 and determine if the selected treatment temperature is within a proper predetermined range, and may generate a "record error" as indicated by block 131 if the selected treatment temperature is out of the proper range, and otherwise may go to block 132 and set various control information to default values, and may also initialize various control variables to suitable pre-ramp state values and set the system state to "SS=PRE-RAMP" in block 133, and then, in block 134, may record information for subsequent debugging processes, in order to provide a record of the error or abnormal condition. The conditions associated with blocks 127 through 134 may be associated with conditions which may need to be recorded to aid subsequent debugging.

If hyperthermia treatment system 1 is not in an idle state, then the program may determine if it is in the ramp-up state, as indicated in decision block 135. If the determination of decision block 135 is affirmative, the program may go to block 136 and may set the system state to a stop condition in order to stop an abandoned ramp-up and may record information of the abandoned ramp-up, and then may go to entry point 124. If the determination of decision block 135 is negative, the program may go to decision block 137 and may determine if hyperthermia treatment system 1 is in the treatment mode, in which case the program may go to block 138, may record the treatment information and may set the system state to a stop condition to stop a treatment mode, and may then go to FIG. 6C via entry point 124. If the determination of decision block 137 is negative, the program may go directly to entry point 124.

If the "button closed" state is detected in decision block 122, the program may go to decision block 139 and, if momentary switch 58 is open, may detect a "button open" condition as the result of a transition from the button closed condition to the button open condition, and may go to block 140 and may set the button state as open, and may then go to entry point 124.

If the state produced by decision block 122 is that the button state register is invalid, then the program may generate a failure shutdown condition, as indicated in block 111A.

Referring to FIG. 6C, in block 150 the program may look at how long a temperature change difference between the present thermocouple temperature and a previous thermocouple temperature has existed, because it is a parameter that may be used in the PID loop. The program may look for a rate of change of thermocouple temperature, and to this end, the program may store a particular number of samples of thermocouple temperature and discard the oldest sample and add the newest one and then take a new average of the stored samples. A time-weighted average may be performed on the temperature difference values, and in block 151, the program may compute a new temperature difference which may be the difference between the last time-weighted average and the present time-weighted average, by excluding the oldest of, for example, 10 measurements being averaged and including the newest measure of temperature difference. From that point, a series of tests may be performed. In decision block 152, the program may determine if the battery voltage is too low for a proper hyperthermia treatment, and if it is, the program may execute a normal shutdown operation, as indicated in block 107. Otherwise, the program may go to decision block 153 and determine if the battery voltage is low but is nevertheless high enough to allow a proper hyperthermia treatment to be performed, and if this decision is affirmative, the program may go to block 154 and count the number of times this condition has been detected (to, for example, ensure that the battery has not failed in the sense of having a single defective cell therein and to ensure that information may be retained for subsequent diagnostic purposes). In decision block 155, the program may compute the thermocouple temperature as measured by two of the A/D converters in microcontroller 40, which may include one with high gain in another with low gain, one having a large temperature range and low resolution and another having a small temperature range with high resolution. If the two temperature measurements are not essentially the same, then the program may go to block 156 and record that information for future diagnostic purposes, to indicate that one of the A/D converter channels may be defective, and also may shut hyperthermia treating unit 1 down. In any case, the program may then go to block 157 and test the power supplies and suitably records the values for use elsewhere in the program (block 110 of FIG. 6A). If the power supplies are properly functional, the program may go to decision block 158 and test the output of the RF circuitry for improper RF output levels, and if an improper RF output level exists, the program may execute a failure shutdown, as indicated in block 111. Otherwise, program may go to decision block 159 and determine if there is an RF short condition. If there is, the program may go to block 160 and set the system state to an error stop condition, and may then go to entry point 161. The program cannot detect an RF runaway condition or an RF shorted condition, if the program is in a stop condition or an idle condition. The determinations of decision blocks 158 and 159 only apply if the program is not in a stop condition or an idle condition. The term "RF runaway condition" means a condition in which the value of the output of the RF circuitry is significantly different than the value "requested" by the previously described feedback circuitry.

Figure 6D:
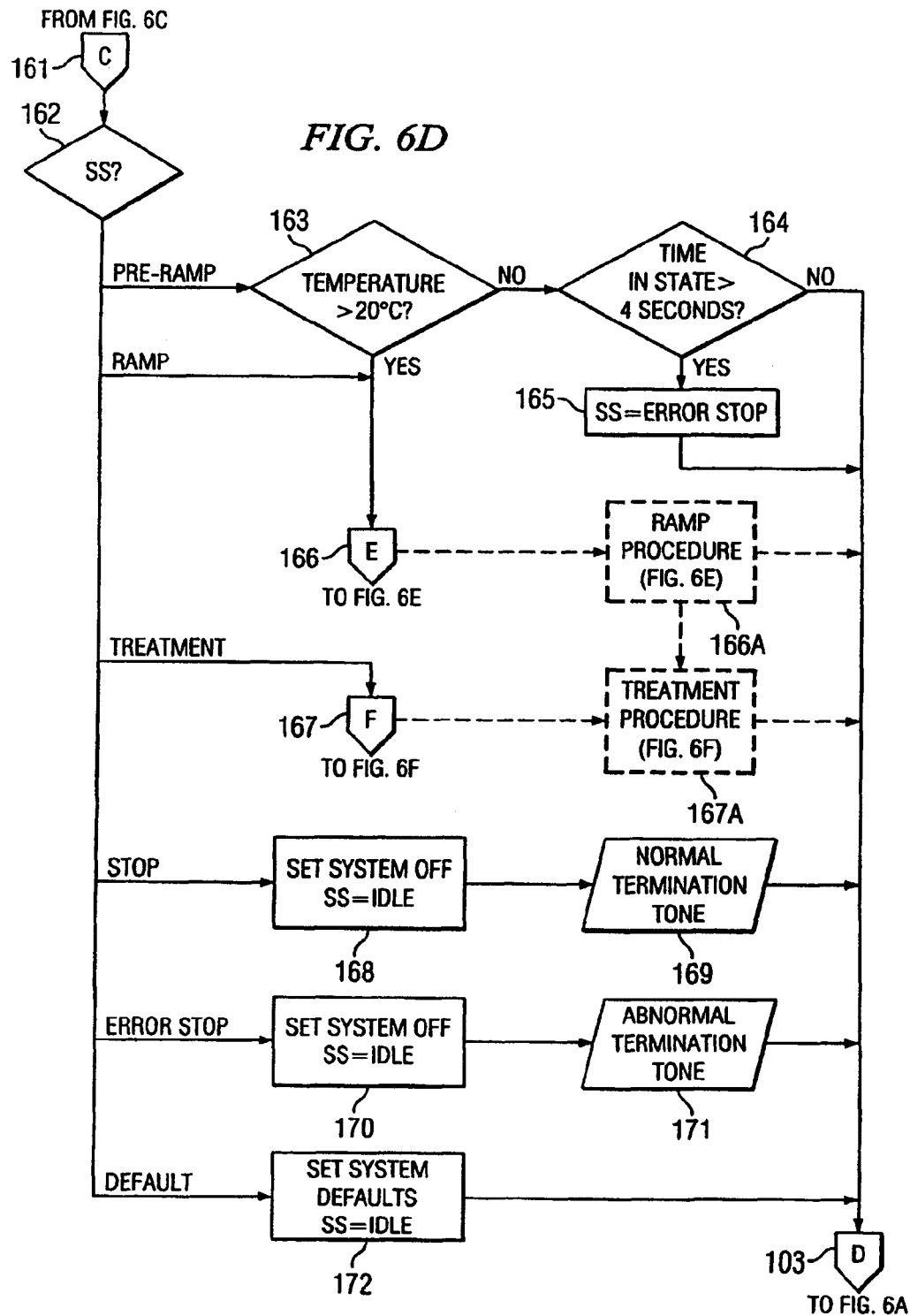

The program then may go to FIG. 6D and enter decision block 162, which may generate one or more codes representing a pre-ramp mode, a ramp mode, a treatment mode, a stop mode, an error stop mode, or a default mode. Decision block 162 represents a multi-state conditional test feature that may determine which of a plurality of conditions hyperthermia treatment unit 1 is in and may generate corresponding codes, one of the plurality of conditions being a default condition which may be represented by a code other than any of the codes representing other conditions. The system may be set to an idle condition if there is a default code which is any code other than the codes representing a first group of conditions shown in FIG. 6D. If the system is in the pre-ramp mode, it may determine if the thermocouple is at a suitable starting temperature, wherein decision block 163 may determine whether the temperature is greater than a predefined value, e.g., 20 degrees Celsius, and if this determination is negative, the program may go to decision block 164 and determine if the thermocouple temperature is less than 20 degrees Celsius for more than a predetermined time, e.g., 4 seconds, and if so, then an error stop condition may be created as indicated in block 165, and the program then may go back to entry point 103 of FIG. 6A. A negative determination of decision block 164 may result in the program returning via entry point 103 to FIG. 6A. If the determination of decision block 163 is affirmative, the program may enter the ramp-up subroutine of FIG. 6E via entry point 166.

Figure 6E:
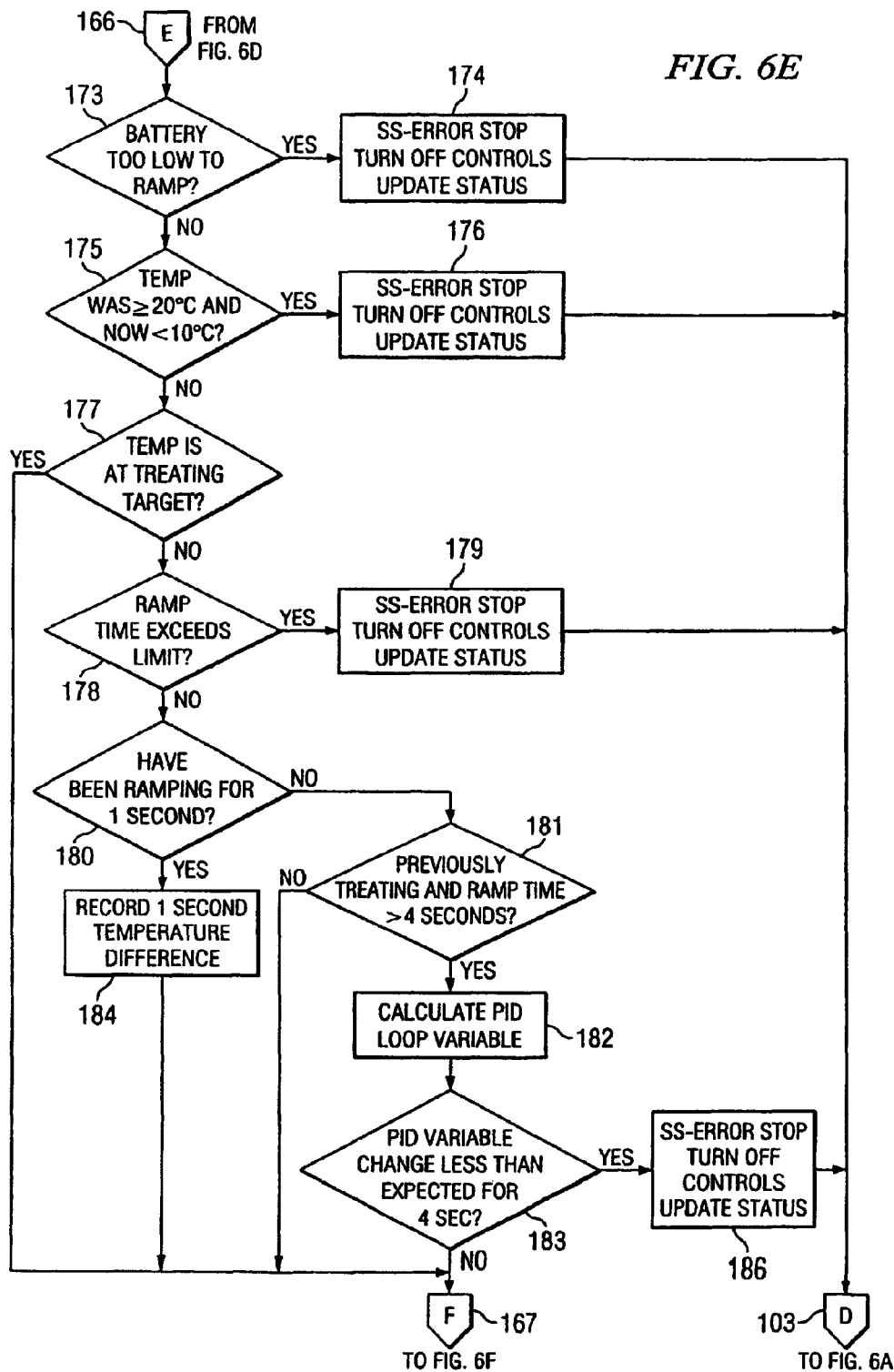

If conditional test decision block 162 determines that hyperthermia treatment system 1 is in the ramp mode, the program may go via entry point 166 to execute the temperature ramp-up procedure shown in detail in FIG. 6E, and represented by block 166A in FIG. 6D. If conditional test decision block 162 determines that hyperthermia treatment system 1 is in the treatment mode, the program may execute the subroutine for executing the treatment temperature maintaining procedure shown in detail in the subroutine of FIG. 6F and also represented in FIG. 6D by block 167A.

If conditional test decision block 162 detects a stop condition, then the program may enter block 168 and set the system to an idle condition, and may also cause speaker 7 to emit a "nominal termination tone" or beeping sound, and then return to FIG. 6A via entry point 103. If conditional test decision block 162 determines that the system is in an error stop condition, the program may reset the system to an off condition as indicated in block 170, and may cause speaker 7 to emit and "abnormal termination tone" as indicated in block 171, and then return to FIG. 6A by way of entry point 103.

Referring to FIG. 6E, a plurality of tests may be performed before beginning the actual temperature ramp-up routine. In block 173 the program may determine if the battery voltage is too low to allow the temperature ramp-up procedure to begin, and if this determination is affirmative, the program may go to block 174 and change the system state to an error stop condition, turn off the various controls, update the status information for subsequent debugging, and then return to FIG. 6A via entry point 103. If the battery voltage is not too low to allow the temperature ramp-up procedure to begin, the program may go to decision block 175 and determine whether the start up thermocouple temperature was greater than or equal to a predetermined value, e.g., 20 degrees Celsius, and also now is less than a predetermined value, e.g., 10 degrees Celsius. If the determination of block 175 is affirmative, the program may go to block 176, set the system state to an error stop condition, turn off appropriate controls, update the debugging status information, and then may go to entry point 103 of FIG. 6A. This test may provide an indication of a possible failure of the thermocouple or an oscillator. If the determination of decision block 175 is negative, the program may begin the temperature ramp-up procedure by determining if the thermocouple temperature is at the selected treatment temperature value, in decision block 177. If this determination is affirmative, the program may go to FIG. 6F via entry point 167 in order to run the PID loop. If the thermocouple temperature is not at the selected treatment temperature, then the program may go to decision block 178 and determine if a predefined maximum ramp time, e.g., of 45 seconds, has been exceeded. If this determination is affirmative, the program may go to block 179 and set the system state to an error stop condition, turn off appropriate controls, update the status information, and go to FIG. 6A via entry point 103. If the maximum ramp time has not been exceeded, then the program may go to decision block 180 and determine if the thermocouple temperature has been ramping upward for a predetermined time, e.g., at least 1 second. If this determination is affirmative, the program may go to block 184 and record the present 1-second temperature difference and then go to FIG. 6F to run the PID loop. If the thermocouple temperature has not been ramping up for a predefined time, e.g., 1 second, the program may go to decision block 181 and determine whether both a previous treatment has been performed and the present ramp time is greater than a predefined time, e.g., 4 seconds. If that is the case, the program may go to block 182 and calculate the various proportional, integral, and differential PID loop variables to thereby update them and then go to decision block 183 and determine if the changes in PID loop variables are less than expected for a predefined time, e.g., 4 second interval. If this determination is affirmative, the program may go to block 186, set the system state to an error stop condition, turn off appropriate controls, and update the debug status information, and then return to FIG. 6A via entry point 103. This portion of the program may determine whether the thermocouple or the RF generator circuitry is defective, by determining if the thermocouple temperature fails to increase during the ramping operation by at least a certain amount of temperature change within a certain amount of time. If the determination of decision block 181 is negative, the program may then go to FIG. 6F via entry point 167 to run the PID loop.

Figure 6F:
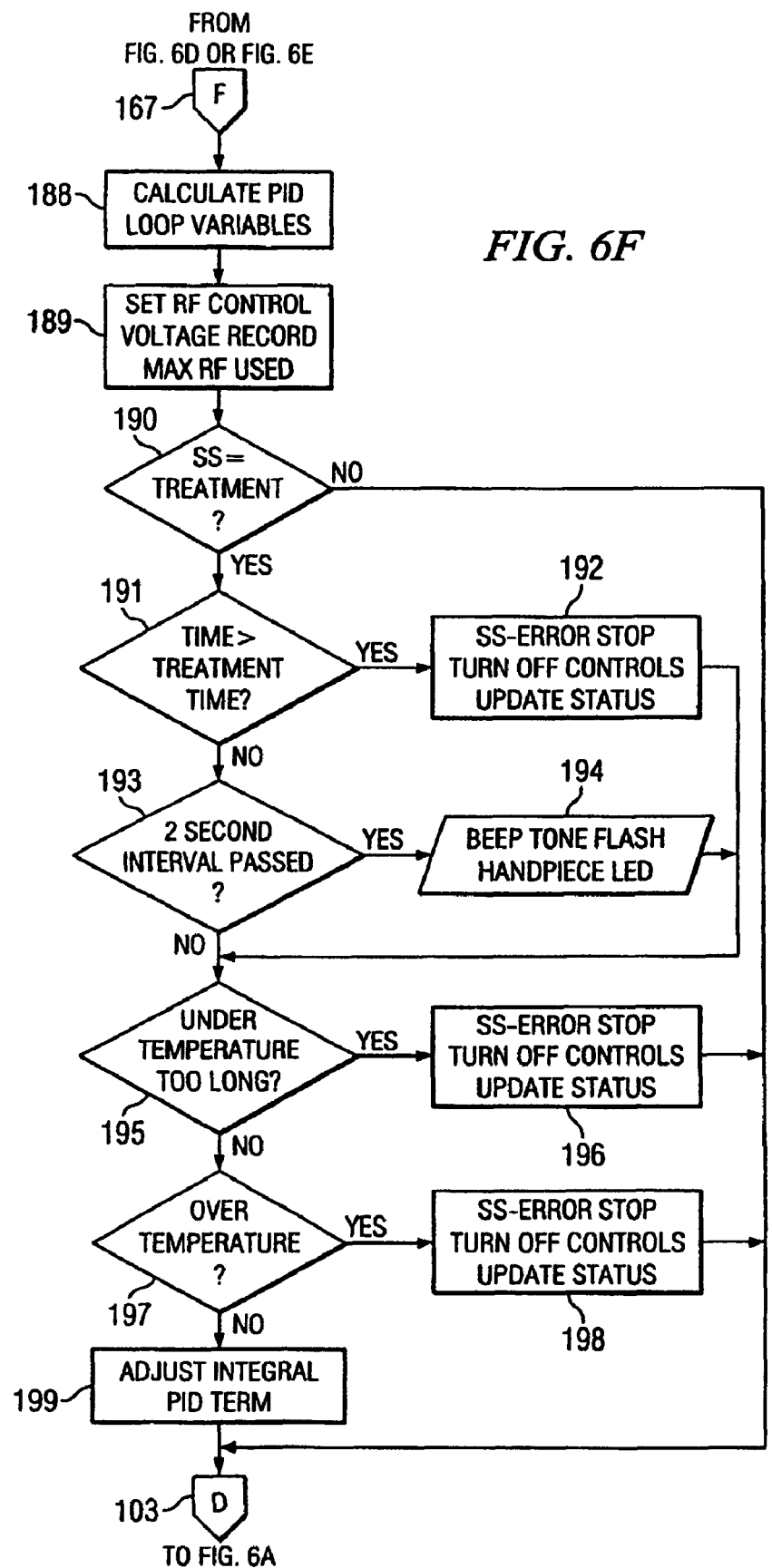

Referring to FIG. 6F, the program may first go to block 188 and calculate PID loop values to determine what the present loop gain should be, and then may go to block 189, set the value of the RF control voltage on conductor 25 (FIG. 4), and record the maximum peak RF voltage produced, for diagnostic purposes. The program may then go to decision block 190 to determine if the system is in the treatment mode. If this determination is negative, the program may still be in the temperature ramp-up mode, and the program may return to FIG. 6A via entry point 103. If the treatment mode has begun, the program may begin a series of tests by going to decision block 191 and determining if the present treatment time exceeds a maximum treatment time e.g., 90 seconds. If this determination is affirmative, the program may go to block 192, set the system state to an error stop condition, turn off appropriate controls, and update the status information, and then go to decision block 195. If the determination of decision block 191 is negative, the program may go to decision block 193 and determine if a predefined time, e.g., 2 second interval, has elapsed. If such time has elapsed, then the program may go to block 184 and produce a beeping tone by means of speaker 7 and cause the handpiece LED 59 (FIG. 3) to flash, to indicate elapsing of consecutive 2 second intervals of treatment time as they occur. In any case, the program may go to decision block 195 and determine if the thermocouple temperature has been below the proper temperature for too long. This may be determined by reference to a stored table of values that determine how execution of the PID loop should progress, in accordance with the earlier discussion herein. If the determination of decision block 195 is affirmative, the program may go to block 196, set the system state to an error stop condition, turn off appropriate controls, update the debugging status information, and then return to FIG. 6A via entry point 103. Otherwise, the program may go to decision block 197 and determine if the thermocouple temperature may be above a maximum permissible temperature, e.g., 58 degree Celsius, and if this determination is affirmative, program may go to block 198 and set the system state to an error stop condition, turn off appropriate controls, update debugging status information, and return to FIG. 6A. Otherwise, the program may go to block 199 and calculate the integral PID terms, meaning that the integral term may be incremented every time the PID loop is executed, wherein the integral term may force the loop gain to appropriately increase as long as the thermocouple temperature is below the selected treatment temperature.

While the invention has been described with reference to several particular embodiments thereof, those skilled in the art will be able to make the various modifications to the described embodiments of the invention without departing from its true spirit and scope. It is intended that all elements or steps which are insubstantially different from those recited in the claims but perform substantially the same functions, respectively, in substantially the same way to achieve the same result as what is claimed are within the scope of the invention. For example, the thermal sensor 29 may not have to be located in either of probes 36A and 36B, and instead could be attached to the applicator 11 in some other fashion so as to thermally contact the treatment site. Also, the oscillator circuitry 19,69 could be included within the RF modulator 21.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of heating tissue with RF energy, comprising:
generating radio frequency (RF) energy;
transmitting the RF energy to the tissue;
measuring temperature of the tissue;
maintaining tissue temperature within a range of a selected temperature for a predetermined treatment time by varying the transmitted RF energy in response to the measured temperature;
terminating treatment at a termination time other than the predetermined treatment time if the measured temperature drifts outside of the range; and
determining the termination time according to a sliding scale.

2. The method of claim 1, wherein according to the sliding scale a predetermined treatment time shortens as the measured temperature drifts further away from the range.

3. The method of claim 1, further including determining the predetermined treatment time according to a thermal dose necessary for treatment of the tissue.

4. The method of claim 1, further including increasing the RF energy during a beginning period of transmitting the RF energy to the tissue.

5. The method of claim 1, further including generating an indicator signal when the tissue temperature reaches a target temperature.

6. The method of claim 1, further including increasing the RF energy in response to the measured temperature.

7. The method of claim 1, further including evaluating a criteria pertaining to a thermal dose delivered to the tissue.

8. A method of treating tissue with RF energy, comprising:
generating radio frequency (RF) energy within a housing;
transmitting the RF energy through a probe to the tissue;
sensing tissue temperature through a thermocouple having a hot junction mounted in the probe and a cold junction compensation circuit coupled to the probe outside the housing;
maintaining tissue temperature within a range of a selected temperature for a predetermined treatment time by varying the transmitted RF energy in response to the sensed tissue temperature;
terminating the treatment at a termination time other than the predetermined treatment time if the sensed tissue temperature drifts outside of the range; and
determining the termination time according to a sliding scale.

9. The method of claim 8, further including determining the predetermined treatment time according to a thermal dose necessary for treatment of the tissue.

10. The method of claim 8, further including increasing the RF energy during a beginning period of transmitting the RF energy.

11. The method of claim 8, further including generating an indicator signal when the tissue temperature reaches a target temperature.

12. The method of claim 8, further including increasing the RF energy in response to the sensed tissue temperature.

13. A method of treating tissue with radio frequency (RF) energy, comprising:
generating RF energy;
transmitting the RF energy to a tissue;
measuring a tissue temperature;
maintaining the tissue temperature within a temperature range during a treatment time by adjusting the RF energy in response to the measured tissue temperature;
adjusting the treatment time according to a sliding scale if the measured tissue temperature varies from the temperature range; and
terminating treatment according to the sliding scale.

14. The method of claim 13, further including determining the treatment time according to a thermal dose necessary for treatment of the tissue.

15. The method of claim 13, further including increasing the RF energy during a beginning period of transmitting the RF energy to the tissue.

16. The method of claim 13, further including generating an indicator signal when the tissue temperature reaches a target temperature.

17. The method of claim 13, further including increasing the RF energy in response to the measured tissue temperature.

18. The method of claim 13, further including evaluating a criteria pertaining to a thermal dose delivered to the tissue.

19. A method of treating tissue with radio frequency (RF) energy, comprising:
generating RF energy;
transmitting the RF energy to a tissue;
measuring a tissue temperature;
maintaining the tissue temperature within a temperature range during a treatment time by adjusting the RF energy in response to the measured tissue temperature; and
terminating treatment according to a sliding scale.

20. The method of claim 19, further including determining the treatment time by a thermal dose necessary for treatment of the tissue.

21. The method of claim 19, further including increasing the RF energy during a beginning period of transmitting the RF energy to the tissue.

22. The method of claim 19, further including generating an indicator signal when the tissue temperature reaches a target temperature.

23. The method of claim 19, further including increasing the RF energy in response to the measured tissue temperature.

24. The method of claim 19, further including evaluating a criteria pertaining to a thermal dose delivered to the tissue.

* * * * *